(12) United States Patent
Murphy et al.

(10) Patent No.: US 11,339,295 B2
(45) Date of Patent: May 24, 2022

(54) OXIDATIVE DYE COUPLERS WITH NOVEL AUXOCHROME SUBSTITUENTS AND AZOMETHINE DYES AND LEUCO FORMS THEREOF

(71) Applicant: WELLA INTERNATIONAL OPERATIONS SWITZERLAND SÀRL, Petit-Lancy (CH)

(72) Inventors: Bryan P. Murphy, Loveland, OH (US); Guiru Zhang, Lebanon, OH (US); Aaron D. Bailey, Vernon Hills, IL (US); Megan E. Bucks, West Chester, OH (US)

(73) Assignee: WELLA INTERNATIONAL OPERATIONS SWITZERLAND SÀRL, Petit-Lancy (CH)

( * ) Notice: Subject to any disclaimer, the term of this patent is extended or adjusted under 35 U.S.C. 154(b) by 0 days.

(21) Appl. No.: 16/487,971

(22) PCT Filed: Aug. 8, 2018

(86) PCT No.: PCT/US2018/045751
§ 371 (c)(1),
(2) Date: Aug. 22, 2019

(87) PCT Pub. No.: WO2019/032671
PCT Pub. Date: Feb. 14, 2019

(65) Prior Publication Data
US 2020/0024455 A1  Jan. 23, 2020

Related U.S. Application Data

(60) Provisional application No. 62/543,747, filed on Aug. 10, 2017.

(51) Int. Cl.
| | | |
|---|---|---|
| *C09B 55/00* | (2006.01) | |
| *A61K 8/41* | (2006.01) | |
| *A61K 8/49* | (2006.01) | |
| *A61Q 5/10* | (2006.01) | |

(52) U.S. Cl.
CPC .............. *C09B 55/00* (2013.01); *A61K 8/413* (2013.01); *A61K 8/492* (2013.01); *A61K 8/4946* (2013.01); *A61Q 5/10* (2013.01); *A61K 2800/4322* (2013.01); *A61K 2800/884* (2013.01)

(58) Field of Classification Search
CPC .......... A61Q 5/10; A61Q 5/065; A61K 8/411; A61K 8/4946; A61K 8/492; A61K 8/413; C09B 55/009; C09B 55/00
USPC .............................................. 8/405, 407, 409
See application file for complete search history.

(56) References Cited

U.S. PATENT DOCUMENTS

| 4,873,338 A | * | 10/1989 | Wiesen | .............. C07D 207/404 546/293 |
| 2010/0275389 A1 | | 11/2010 | Fadli et al. | |

FOREIGN PATENT DOCUMENTS

WO   WO-2019032671 A1   2/2019

OTHER PUBLICATIONS

STIC Search Report dated May 27, 2020.*
"International Application Serial No. PCT/US2018/045751, International Search Report dated Nov. 20, 2018", 5 pgs.
"International Application Serial No. PCT/US2018/045751, Written Opinion dated Nov. 20, 2018", 9 pgs.
Pankina, Olga Yu, et al., "Condensation of amino derivatives of benzimidazol-2-ones and imidazo[4,5-b]pyridin-2-ones with 2,6-dimethyl-[gamma]-pyrone in acetic acid", Russian Journal of Organic Chemistry, vol. 49, No. 5, (Jun. 8, 2013), 779-781.
Yamamoto, Yumi, et al., "Isomeric iodinated analogs of nimesulide: Synthesis, physicochemical charachterization,cyclooxygenase-2 inhibitory activity, and transport across Caco-2 cells", Bioorganic and Medicinal Chemistry 24(16), (Jun. 7, 2016), 3727-3733.
Zhang, Guiru, et al., "A new class of oxazolidinone- and phthalimide-based oxidation dye couplers and their effect on azomethine dye color", Dyes and Pigments, vol. 149, (Sep. 22, 2017), 167-176.
"International Application Serial No. PCT/US2018/045751, International Preliminary Report on Patentability dated Feb. 20, 2020", 11 pgs.

* cited by examiner

*Primary Examiner* — Eisa B Elhilo
(74) *Attorney, Agent, or Firm* — Victoria Friedman; Dennemeyer & Associates, LLC

(57) ABSTRACT

The present invention concerns an auxochrome substituent for an oxidative dye coupler. The auxochrome substituent enables ready developer reaction with the coupler to form azomethine and leuco dyes. Manipulation of the auxochrome substituent enables a bathochromic or hypsochromic shift of the light absorbance by the azomethine dye formed with the auxochrome substituted coupler.

28 Claims, No Drawings

OXIDATIVE DYE COUPLERS WITH NOVEL AUXOCHROME SUBSTITUENTS AND AZOMETHINE DYES AND LEUCO FORMS THEREOF

CLAIM OF PRIORITY

This patent application is a U.S. National Stage Filing under 35 U.S.C. 371 from International Application No. PCT/US2018/045751, filed on Aug. 8, 2018, and published as WO 2019/032671 on Feb. 14, 2019, which claims the benefit of priority to U.S. Provisional Application Ser. No. 62/543,747, filed Aug. 10, 2017, which are incorporated by reference herein in their entirety.

FIELD OF THE INVENTION

The present invention concerns an auxochrome substituent for an oxidative dye coupler. The substituent is formulated with an amide, imide, carbamate or hydrazide moiety which can be converted into an electron donating group. The auxochrome substituent enables ready developer reaction with the coupler to form azomethine and leuco dyes. Maintaining the auxochrome substituent or converting it respectively causes a bathochromic or hypsochromic shift of the light absorbance by the chromophoric dye.

BACKGROUND OF THE INVENTION

The permanent alteration of the hair color by the application of hair dyes is well known. In order to provide the consumer with the shade and the intensity of color desired, a complex chemical process is utilized. Permanent hair dyeing formulations typically involve oxidative hair dye precursors, which can diffuse into the hair through the cuticle and into the cortex where they then react with each other and a suitable oxidizing agent to form the end dye molecules. Due to their larger size, the resultant molecules are unable to readily diffuse out of the hair during subsequent washing with water and/or detergents; hence delivering a consumer-desired permanency of color. This reaction typically takes place in an aggressive environment at approximately pH 10 in the presence of an alkalizing agent and an oxidizing agent. Typically, an oxidizing composition includes a developer or primary component, a coupler or secondary component and an oxidizing component. The developer and coupler are precursors of the dye composition and are kept separate from the oxidizing component until just before use. Combination of the precursors (developer and coupler) and oxidizing component results in in situ formation of an azomethine dye which is immediately applied to the hair. Alternatively, the oxidizing composition is a leuco dye composition and an oxidizing component. The leuco dye composition is the reduced form of the azomethine dye and can be preformulated as such rather than prepared immediately prior to use. An alkalizing agent is also mixed with the oxidizing composition shortly before use. The consumer repeats this process regularly in order to maintain the desired hair color and shade and the intensity of color and to ensure continual, even coverage of the hair including coverage of new hair growth.

SUMMARY OF THE INVENTION

The present invention is directed to aspects of azomethine and leuco dyes that enable chemical manipulation of bathochromic and hypsochromic shifts of the color of the dyes. One aspect of the present invention is directed to an auxochrome of an azomethine or leuco dye that enables such shifts. Another aspect of the present invention is directed to a coupler substituted by embodiments of the auxochrome. Another aspect of the present invention is directed to an azomethine or leuco dye having a coupler component substituted by embodiments of the auxochrome. A further aspect of the present invention is directed to a kit of receptacles, containers, bottles, vials, tubes or vessels containing a) an oxidizer composition and bi) the azomethine precursors of a coupler and developer or bii) a leuco dye wherein the coupler of the azomethine precursors or the coupler component of the leuco dye is substituted by the auxochrome embodiment. Another aspect of the present invention is directed to a method for dying keratin fibers such as human hair using the kit aspect to formulate an azomethine or leuco dye aspect of the invention and apply to the keratin fibers.

Embodiments of the auxochrome include groups such as amides, imides, carbamates and/or hydrazides and can be positioned on the coupler portion (acceptor component) of the azomethine or leuco dye. These embodiments are structured as linear and cyclic moieties with functional groups according to any one of Formulas A, B, C and D:

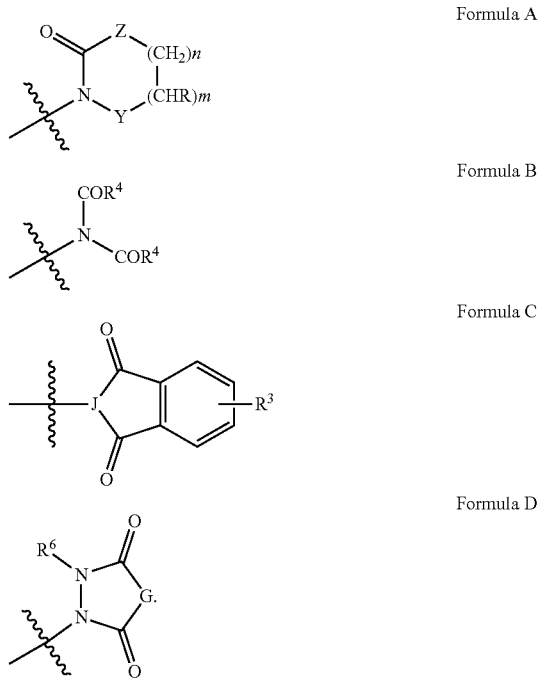

For Formulas A, B, C and D, the atom designators Y, Z, J and G are as follows: Y is carbonyl (C=O) or methylenyl ($CH_2$). Z is oxygen (O), methylenyl, or substituted or unsubstituted vinyl (—$R^2C$=$CR^2$—). J is nitrogen (N), or hydrazo (—N—$NR^6$—). G is optionally substituted multimethylenyl (($CHR^6)_p$) or substituted or unsubstituted vinyl (—$R^2C$=$CR^2$—). The R substituents for Formulas A-D are hydrogen or one of an alkyl, alkoxy, alkylalkoxy, alkoxyalky, hydroxyalkyl, alkylamino or aminoalkyl group wherein the alkyl, alkoxy, hydroxyalkyl, aminoalkyl and alkylamino groups are linear, branched or cyclic and include 1 to 6 carbons for the linear or branched groups and 3 to 6 carbons for the cyclic groups.

For these Formulas, the integer designators m, n and p are as follows: m is zero or an integer of 1 to 6. n is zero or an integer of 1 to 6. P is an integer of 1 to 3.

The squiggle bond indicated by

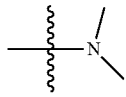

is the bond that connects the auxochrome with the coupler or with the coupler component of the azomethine or leuco dye.

The auxochrome substituent can function as an electron withdrawing group for the coupler component of an azomethine dye or leuco dye and when an appropriate auxochrome is opened, the opened congener can function as an electron donating group for the coupler component of an azomethine dye or leuco dye.

The embodiments of the auxochrome can be a substituent of the precursor aspect of an azomethine dye or leuco dye. More specifically, the auxochrome embodiments can be substituted on a coupler embodiment. The coupler embodiment with auxochrome can be oxidatively coupled with developer to form an azomethine dye or subsequently reduced to form a leuco dye. The coupler embodiment is typically a known aromatic or heteroaromatic compound that is primarily substituted at least by a hydroxyl or a primary amino group and optionally by an alkyl, alkoxy, alkylalkoxy, alkoxyalkyl, hydroxyalkyl, amino, aminoalkyl or alkylamino group wherein the alkyl and alkoxy moieties can be linear or branched with 1 to 6 carbons or cyclic with 3 to 6 carbons. The aromatic or heteroaromatic core of the coupler can be phenyl, pyridinyl, pyrimidinyl, furanyl, thiophenyl, pyrrolyl, imidazolyl, indolyl, benzimidazolyl, benzothiazolyl, benzomorpholinyl, naphthalenyl, quinolinyl, quinazolinyl, and similar 5 member aromatic rings, 6 member aromatic rings, 5:6 member bicyclic aromatic rings, 6:6 member bicyclic aromatic rings that are carbon and one, two or three nitrogen, oxygen and/or sulfur groups. The preferred coupler core includes a phenyl, pyridinyl, benzomorpholino, indolyl or benzimidazolyl core. The primary substituent of the coupler is positioned para to the location on the coupler where the developer will bond to form the azomethine or leuco dye molecule. The auxochrome can be positioned at any other location of the aromatic or heteroaromatic core of the coupler and typically is located in a meta position relative to the location on the coupler where the developer will bond.

The other precursor of an azomethine or leuco dye is the developer. The developer can be an aromatic or heteroaromatic compound substituted by a primary amine ($NH_2$) and by either an optionally substituted amino group or a hydroxyl group para to the primary amine. The aromatic or heteroaromatic core of the developer can be phenyl, pyridinyl, pyrimidinyl, furanyl, thiophenyl, pyrrolyl, imidazolyl, indolyl, benzimidazolyl, benzothiazolyl, naphthalenyl, benzozazinyl, quinolinyl, quinazolinyl, and similar 5 member aromatic and dihydro aromatic rings, 6 member aromatic and dihydroaromatic rings, 5:5 member bicyclic aromatic and dihydroaromatic rings 5:6 member bicyclic aromatic and dihydroaromatic rings, 6:6 member bicyclic aromatic and dihydro aromatic rings that are carbon and one, two or three nitrogen, oxygen and/or sulfur groups. The preferred developer cores include phenyl, pyrazolyl, benzimidazolyl, pyrrolopyridinyl, benzoxazinyl and dihydropyrazolopyrazolonyl.

An additional aspect of the invention is a kit composed of embodiments of the azomethine dye precursor aspects of the invention in one container, bottle, vessel, vial, tube or receptacle and an oxidizer composition in another container. The kit aspect alternatively is composed of the leuco dye aspect of the invention in one container and an oxidizing composition in another container. Additional excipients can be included in the containers of the kit.

Another aspect of the invention concerns a method for dying keratin fibers. For dying with an azomethine dye, the kit with the azomethine precursors and oxidizer composition are combined immediately before use. The combined composition is applied to keratin fibers such as human hair, allowed to remain on the hair for an appropriate time to allow the dye to penetrate the cortex of the fibers and then the keratin fibers are rinsed and dried. For dying with a leuco dye, the leuco dye composition is applied to keratin fibers such as human hair and then following an appropriate period of time to allow absorption of the leuco dye into the keratin fiber the oxidizer composition is applied. The oxidizer converts the colorless leuco dye into a colored dye by converting the amine bridge between the developer and coupler components of the leuco dye into an imine group otherwise known as an azomethine group or Schiff base.

The keratin fibers can be prepared for dying by washing or shampooing the fibers and drying them to dampness. The keratin fibers can optionally be bleached by known techniques to remove natural color that may interfere, modify or dull the color of the applied dye.

DETAILED DESCRIPTION OF THE INVENTION

Definitions

As used herein the term "hair" to be treated may be "living" i.e. on a living body or may be "non-living" i.e. in a wig, hairpiece or other aggregation of non-living keratinous fibers. Mammalian, preferably human hair is preferred. However wool, fur and other keratin containing fibers are suitable substrates for the compositions according to the present invention.

The term "keratin fibers" means bundles of macrofibrils of the cortical or center region of a strand of hair. The macrofibrils are made of multiple filamentous protein strands known as a keratins that contain abundant cysteine disulphide bridges providing strength and rigidity to the strands. The macrofibrils constitute the region of a hair strand where it is believed that externally applied dyes take up permanent residence.

By "hair coloring" composition it is meant a composition suitable for changing the color of hair. The hair coloring composition is referred hereinafter as "the composition", unless otherwise specified. The hair coloring composition can comprise oxidative dye precursors, direct dyes or even no, or substantially no, dyes in case of bleaching only compositions where the change of color is mainly caused by the degradation of the natural melanin contained in the hair shaft by the oxidizing agent. The term "hair coloring" composition as used herein covers hair bleaching and hair oxidative dyeing products.

All percentages are by weight of the hair coloring composition, i.e. of the ready-to-use composition, unless otherwise specified. When more than one composition is used during a treatment, the total weight to be considered is the total weight of all the compositions applied on the hair simultaneously (i.e. the weight found "on head"), typically resulting from mixing an oxidative composition (also called developer and/or oxidizing composition/component) with a dye composition (also called tint, and/or dye composition/component), unless otherwise specified. All ratios or percentages are weight ratios or weight percentages unless specifically stated otherwise.

As used herein and in the appended claims, the singular forms "a," "an" and "the" include plural referents unless the context clearly dictates otherwise.

The term "about" as used herein, when referring to a numerical value or range, allows for a degree of variability in the value or range, for example, within 10%, or within 5% of a stated value or of a stated limit of a range.

The term "may" in the present context means "is permitted to" or "is able to" and is a synonym for the term "can." The term "may" as used herein does not mean possibility or chance.

The term "and/or" means both or all of the items together to which these conjunctions refer and well as each of the items alone and separate from the others. When more than two items are referred, the term and/or also means any combination of these multiple items as well as all and each.

The term "substantial" means a significant amount such as more than a majority amount. For example, a mixture of compounds A and B in which A is present in a substantial amount means that A is present at a weight percent or number of moles that is greater than the weight percent or number of moles of B. This term also means more than a minimal characteristic, examples of which include substantial flow or substantial color or substantial treatment.

COMPOSITIONS AND FORMULATIONS

The auxochrome substituted coupler embodiments of the present invention are oxidation dye couplers suitable for forming an azomethine dye or a leuco dye. The auxochrome substituent has the capability of functioning as an electron withdrawing group and when unmasked, is capable of functioning as an electron donating group. These capabilities respectively facilitate bathochromic and hypsochromic color shifts of the resulting azomethine and leuco dyes formed by oxidative combination of the auxochrome substituted coupler and developer. In the field of oxidative dyes a developer and coupler are also generally known respectively as primary and secondary intermediates or donor (developer, donates the azomethine group) and acceptor (coupler, accepts azomethine group) components. Their combination just prior to oxidation is also known as a tint composition.

Auxochrome Substituted Coupler Embodiments

These auxochrome substituted coupler embodiments comprise a compound of Formula I

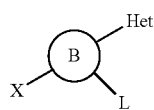

Formula I

Formula I may be prepared from any one of many suitable, known couplers by addition of the Het group. Suitable couplers to which the Het group may be added are described below. A preferred group of couplers is also described. The Het group is the auxochrome embodiment described above and is repeated as follows.

The group Het is the embodiment of the auxochrome and is a cyclic aliphatic or aromatic amide, cyclic carbamate, cyclic hydrazide or a cyclic or linear imide, each with optional substituents. Het is selected from Formula A, B, C or D:

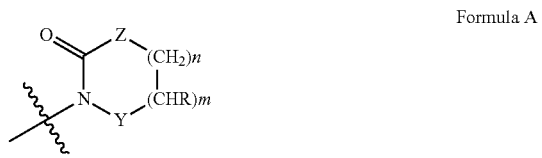

Formula A

Formula B

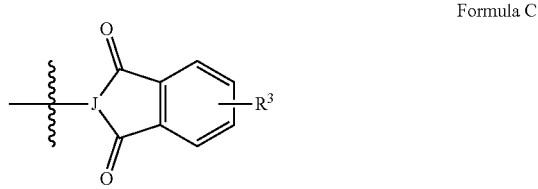

Formula C

Formula D

The atom designators R, $R^3$, $R^4$, $R^6$, Y, Z, J and G for Formulas A-D provide functional and/or hydrocarbon and/or substituted hydrocarbon groups. The atom designator Y is carbonyl or methylenyl.

Each of the atom designators R independently is hydrogen, linear or branched alkyl of 1 to 6 carbons, cyclic alkyl of 3 to 6 carbons, linear or branched alkoxy of 1 to 6 carbons, alkylalkoxy of 1 to 4 carbons in the alkyl group and 1 to 4 carbons in the alkoxy group, alkoxyalkyl of 1 to 4 carbons in the alkyl group and 1 to 4 carbons in the alkoxy group, alkylamino of 1 to 4 carbons in the alkyl group or aminoalkyl of 1 to 4 carbons in the alkyl group.

Each of the atom designators $R^3$ independently is hydrogen, a linear or branched alkyl of 1 to 6 carbons or a cyclic alkyl of 3 to 6 carbons.

Each of the atom designators $R^4$ independently is a linear, branched alkyl of 1 to 6 carbons, a cyclic alkyl of 3 to 6 carbons, a linear or branched hydroxyalkyl of 1 to 6 carbons, a cyclic hydroxyalkyl of 3 to 6 carbons, phenyl, toluenyl or pyridinyl.

The atom designator Z is oxygen, methylenyl ($CH_2$), or optionally substituted vinyl of the formula —$R^2C$=$CR^2$— wherein each $R^2$ is independently is hydrogen, linear or branched alkyl of 1 to 6 carbons, cyclic alkyl of 3 to 6 carbons, linear or branched alkoxy of 1 to 6 carbons, alkylalkoxy of 1 to 4 carbons in the alkyl group and 1 to 4 carbons in the alkoxy group, alkoxyalkyl of 1 to 4 carbons in the alkyl group and 1 to 4 carbons in the alkoxy group, alkylamino of 1 to 4 carbons in the alkyl group or aminoalkyl of 1 to 4 carbons in the alkyl group.

The atom designator J is nitrogen or hydrazo of the formula —N—NR$^6$— wherein each R$^6$ independently is hydrogen, methyl or ethyl.

The atom designator G is an optionally substituted vinyl group of the formula —R$^2$C=CR$^2$— wherein R$^2$ is the same as recited for the atom designator Z, or a multi methylenyl or substituted multimethylenyl group of the formula (CHR$^6$)$_p$ wherein each R$^6$ independently is hydrogen, methyl or ethyl.

Each of the integer designators m and n independently is zero or an integer of 1 to 6. The integer designator p is an integer of 1 to 3.

A proviso applies to the integer designators m and n such that at least one of m and n is 1 unless Z is —R$^2$C=CR$^2$—.

The squiggle bond of Het indicates the bond between Het and the B aromatic ring.

The suitable couplers useful for forming Formula I include the following compounds in which the atom designators L and X as well as optional additional substituents are specified. Included are resorcinol, 4-chlororesorcinol, 2-chlororesorcinol, 2-methylresorcinol, 4,6-dichlorobenzene-1,3-diol, 2,4-dimethylbenzene-1,3-diol, m-aminophenol, 4-amino-2-hydroxytoluene, 2-methyl-5-hydroxyethyl-aminophenol, 3-amino-2,6-dimethylphenol, 3-amino-2,4-dichlorophenol, 5-amino-6-chloro-o-cresol, 5-amino-4-chloro-o-cresol, 6-hydroxybenzomorpholine, 2-amino-5-ethylphenol, 2-amino-5-phenylphenol, 2-amino-5-methylphenol, 2-amino-6-methylphenol, 2-amino-5-ethoxyphenol, 5-methyl-2-(methylamino)phenol, 2,4-diaminophenoxyethanol, 2-amino-4-hydroxyethylaminoanisole, 1,3-bis-(2,4-diaminophenoxy)-propane, 2,2'-(2-methyl-1,3-phenylene)bis(azanediyl) diethanol, benzene-1,3-diamine, 2,2'-(4,6-diamino-1,3-phenylene)bis(oxy)diethanol, 3-(pyrrolidin-1-yl)aniline, 1-(3-(dimethylamino)phenyl)urea, 1-(3-aminophenyl)urea, 1-naphthol, 2-methyl-1-naphthol, 1,5-naphthalenediol, 2,7-naphthalenediol or 1-acetoxy-2-methylnaphthalene, 4-chloro-2-methylnaphthalen-1-ol, 4-methoxy-2-methyl-naphthalen-1-ol, 2,6-dihydroxy-3,4-dimethylpyridine, 2,6-dimethoxy-3,5-pyridinediamine, 3-amino-2-methylamino-6-methoxypyridine, 2-amino-3-hydroxypyridine, 2,6-diaminopyridine, pyridine-2,6-diol, 5,6-dihydroxyindole, 6-hydroxyindole, 5,6-dihydroxyindoline, 3-methyl-1-phenyl-1H-pyrazol-5(4H)-one, 1,2,4-trihydroxybenzene, 2-(benzo[d][1,3]dioxol-5-ylamino)ethanol (also known as hydroxyethyl-3,4-methylenedioxyaniline), and mixtures thereof. Also included are 4,5 methylenedioxyphenol, bis-pyrazole, pyrazoline-3,5-di one, 3-aminopyrazoline, pyrazolo[1,5-b]1,2,4-triazole, pyrazolo[3,2-c]-1,2,4-triazole, pyrazolo[1,5-e]tetrazole, pyrazolo[1,5-b]pyrazole, pyrazolo [1,2-a]pyrazol-1 (5H)-one, imidazo[1,2-b-]pyrazole, pyrazolo[1,5-e]-1,2,4-triazole, pyrazolo[3,4-d]thiazole, pyrazolo [5,1-c]-1,2,4-triazole, pyrazolo[1,5-a]pyrimidi-5-one, pyrazolo[1,5-a]pyrimidin-7-one, 4-phenylpyrrolo[3,2-d] oxazoloe, imidazo[5,1-b]thiazol-3(2H)-one, thazolo[3,2-b] [1,2,4]triazol-6(5H)-one, imidazole[3,2-a]imidazole, imidazole[1,2-b]-1,2,4-triazole, imidazole[2,1-c]-1,2,3-triazole, hydroxyimidazo[1,2-a]pyridine, aminoimidazo[1,2-a]pyridine, N-substituted 4-hydroxyindoline, 5,6-dihydroxyindoline, 2-iminoindoline, indazolamine, 1H-perimidine and 2,3dihydroperimidine.

Preferable couplers are those of Formula I wherein the B ring is an aromatic ring selected from the group consisting of phenyl, pyridinyl, benzomorpholinyl, benzimidazolyl and indolyl. For these preferred couplers, the atom designator X is H, OH, NH$_2$ or NR$^1$H wherein R$^1$ may be hydrogen, methyl or ethyl. The atom designator L is OR$^5$ wherein R$^5$ is hydrogen for the finished coupler of Formula I and may also be a hydroxyl protecting group during the synthesis of the compound of Formula I. These preferred couplers include the Het group as described above.

Specific embodiments of Formula I include Formulas IA through IE wherein each R" independently is hydrogen, a linear, branched alkyl of 1 to 6 carbons, a cyclic alkyl of 3 to 6 carbons, a linear or branched hydroxyalkyl of 1 to 6 carbons, a cyclic hydroxyalkyl of 3 to 6 carbons or phenyl.

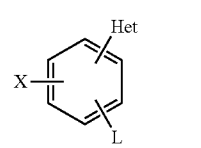

IA

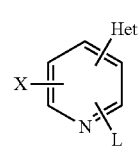

IB

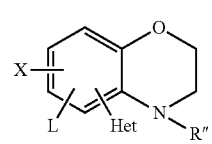

IC

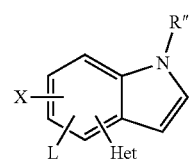

ID

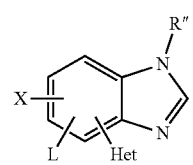

IE

The positions of L, X and Het may be arranged to be at any location around the aromatic rings of Formulas IA-IE provided that L is para to the desired site of developer attachment. Preferably also X and Het are bonded to the phenyl or benzo ring. The preferred sites of attachment of L, X and Het are shown by the following primed Formulas of IA-IE, IA', IB', IC', ID' and IE'

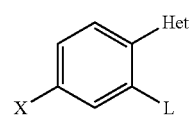

IA'

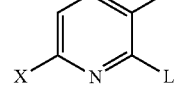

IB'

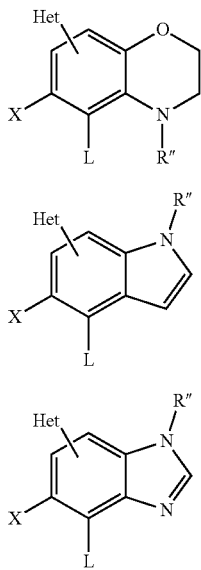

More preferred couplers include those of Formulas IA, IB or ID especially IA', IB' and ID'. Of these, Formulas IA and IA' are preferred with Het as Formula A, Formula C or Formula D. Especially more preferred are couplers IA and IA' with Het as Formula A. Preferred atom designators for the especially more preferred couplers with Het as Formula A are Z as O or $CH_2$; m as zero or 1 and n as zero or 1 wherein the sum of m and n is 1 or 2. Most preferred versions of couplers of Formulas IA and IA' have: a) Het as Formula A, Z as O, m as zero and n as 1; b) Het as Formula C; c) Het as phthalimidyl; and
d) Het as

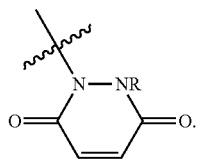

Developer Component

The developer component suitable for forming an azomethine dye and/or a leuco dye with a coupler of Formula I includes compounds of Formula III wherein A is an aromatic or heteroaromatic ring:

Formula III

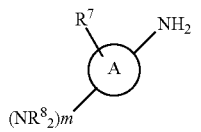

For Formula III, the atom designators $R^7$ and $(NR^8_2)_m$ can provide some of the optional substituents of the suitable aromatic amines that can function as developers. Suitable aromatic amines which include substituents such as but are not limited to the foregoing atom designators, are: toluene-2,5-diamine, p-phenylenediamine. N-phenyl-p-phenylenediamine, N,N-bis(2-hydroxyethyl)-p-phenylenediamine, 2-hydroxyethyl-p-phenylenediamine, hydroxypropyl-bis-(N-hydroxyethyl-p-phenylenediamine), 2-methoxymethyl-p-phenylenediamine, 2-(1,2-dihydroxyethyl)-p-phenylenediamine, 2,2'-(2-(4-aminophenylamino)ethylazanediyl) diethanol, 2-(2,5-diamino-4-methoxyphenyl)propane-1,3-diol, 2-(7-amino-2H-benzo[b][1,4]oxazin-4(3H)-yl)ethanol, 2-chloro-p-phenylenediamine, p-aminophenol, p-(methylamino)phenol, 4-amino-m-cresol, 6-amino-m-cresol, 5-ethyl-o-aminophenol, 2-methoxy-p-phenylenediamine, 2,2'-methylenebis-4-aminophenol, 2,4,5,6-tetraminopyrimidine, 2,5,6-triamino-4-pyrimidinol, 1-hydroxyethyl-4,5-diaminopyrazole sulfate, 4,5-diamino-1-methylpyrazole, 4,5-diamino-1-ethylpyrazole, 4,5-diamino-1-isopropylpyrazole, 4,5-diamino-1-butylpyrazole, 4,5-diamino-1-pentylpyrazole, 4,5-diamino-1-benzylpyrazole, 2,3-diamino-6,7-dihydropyrazolo[1,2-a]pyrazol-1(5H)-one dimethosulfonate, 4,5-diamino-1-hexylpyrazole, 4,5-diamino-1-heptylpyrazole, methoxymethyl-1,4-diaminobenzene, N,N-bis(2-hydroxyethyl)-N-(4-aminophenyl)-1,2-diaminothane, 2-[(3-aminopyrazolo[1,5-a]pyridin-2-yl)oxy]ethanol hydrochloride, 2-hydroxy-1,3-bis-(N-2-hydroxyethyl-4-aminophenylamino)propane, bis-(2,4-diaminophenyl) alkanes and alkanols of 1 to 4 carbons of the alkane or alkanol group, 2,4,5,6 tetraaminopyrimidine, triaminopyrimidine, triaminopyrimidinone, salts thereof and mixtures thereof. Additional developer aromatic amines which may optionally substituted by the atom designators $R^7$ and $(NR^8_2)_m$ include naphthalenyl amine, pyrimidinyl amine, benzoxazinyl amine, pyrazolyl amine, benzimidazolyl amine, pyrrolpyridinyl amine, dihydroprazolopyrazolonyl amine, quinolinyl amine, quinazolinyl amine, benzothiophenyl amine, benzofuranyl amine and indolyl amine.

Preferred embodiments of Formula III include those in which the aromatic core symbolized by A in the circle is phenyl, pyrazolyl, benzimidazolyl, pyrrolopyrimidinyl, benzoxazinyl or dihydropyrazolopyrazolonyl. The preferred embodiments also include $R^7$ as hydrogen, hydroxyl, linear or branched alkyl of 1 to 6 carbons, cyclic alkyl of 3 to 6 carbons, linear or branched hydroxyalkyl of 1 to 6 carbons, cyclic hydroxyalkyl of 3 to 6 carbons, linear or branched alkoxy of 1 to 6 carbons, cyclic alkoxy of 3 to 6 carbons, linear or branched alkoxyalkyl of 1 to 4 carbons in the alkoxy group and 1 to 4 carbons in the alkyl group, cyclic alkoxyalkyl of 1 to 4 carbons in the alkoxy group and 3 to 6 carbons in the alkyl group, or linear or branched hydroxyalkoxy of 1 to 6 carbons in the alkoxy group; each $R^8$ independently is hydrogen, hydroxyalkyl of 1 to 4 carbons, N,N-di-(hydroxyalkyl)aminoalkyl of 1 to 3 carbons in each hydroxyalkyl group and 1 to 3 carbons in the alkyl group and m is zero or one.

More preferred embodiments of Formula III individually include each of the aromatic cores described above as preferred aromatic cores. Especially preferred embodiments of Formula III include those in which A is phenyl, pyrazolyl, benzimidazolyl or dihydropyrazolopyrazolonyl. More especially preferred embodiments of Formula III include those in which A is phenyl, pyrazolyl or dihydropyrazolopyrazolonyl. Most especially preferred embodiments of Formula III include phenyl or pyrazolyl.

For each of the foregoing preferences, a preferred m is zero when $R^7$ is OH. Alternatively, when m is 1, $R^7$ is other than OH and at least one of $R^8$ is hydrogen.

Specific embodiments of Formula III include Formulas IV-VIII:

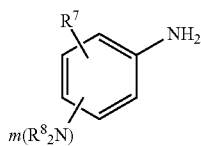

Formula IV

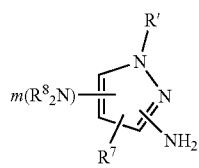

Formula V

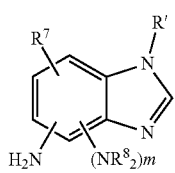

Formula VI

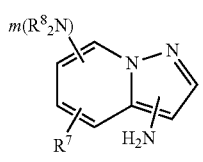

Formula VII

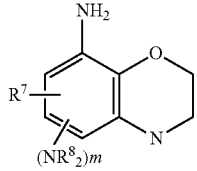

Formula VIII

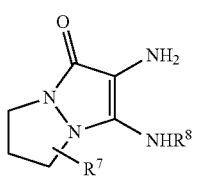

Formula IX

For Formulas IV-IX, the pairs of groups: a) $NH_2$ and $R^7$ as OH and b) $NH_2$ and $R^8_2N$ are positioned on Formulas IV-IX at any position relative to each other except a meta position and the group $R^7$ or $R^8_2N$ that is not part of the pair is positioned at any other position on the A ring.

Specific developer compounds include Formulas PAP, Bis, PPD, Alkoxy PPD, Amino pyrazole, hexyl pyrazole, Pyrrolopyridine, Hydroxy PPD, Benzomopholine PPD, Methoxy, hydroxyl PPD and dihydro PPZO, wherein $R^{iii}$ of Benzomopholine PPD is hydrogen, alkyl of 1 to 4 carbons or phenyl and $R^{iv}$ of Benzomopholine PPD is hydrogen, alkyl of 1 to 4 carbons, alkoxy of 1 to 4 carbons, alkylalkoxy of 1 to 4 carbons in each of the alkyl and alkoxy groups, or hydroxyalkyl of 1 to 4 carbons in the alkyl group.

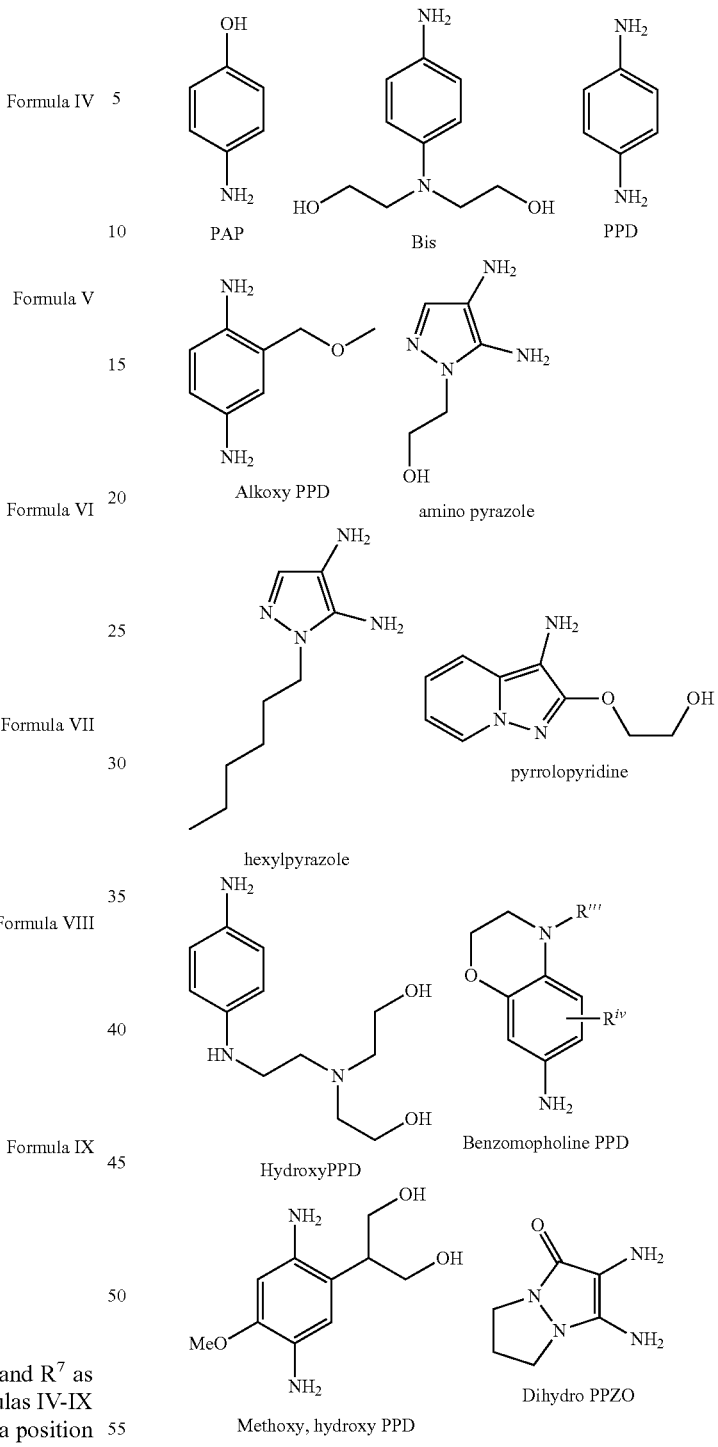

Azomethine Dye and Leuco Dye

The azomethine dye or leuco dye embodiments of the present invention are prepared by combining the developer and auxochrome substituted coupler embodiments of the invention under conditions to cause aromatic electrophilic substitution of the developer onto the coupler and a) form the azomethine dye having an imine bridging group or b) form the leuco due having an amine bridging group. Typically, the azomethine dye is prepared by in situ combining the contents of the two containers of the azomethine dye kit. In this context, in situ means combining the contents of the two containers shortly before use to dye keratin fibers such as human hair.

The leuco dye is the reduced form of the azomethine dye and is prepared by first forming the azomethine dye and then reducing it with sodium dithionite, hydroxyacetone and/or hydrogen. The leuco dye is a stable form of the oxidatively formed reaction product of the developer and auxochrome substituted coupler embodiments of the present invention. Typically, the kit container of the first composition of leuco dye is first applied to keratin fibers and the second composition is then applied to obtain oxidation of the leuco dye to a colored compound.

The azomethine dye and leuco dye embodiments of the invention are characterized respectively by Formula IIa and Formula IIb

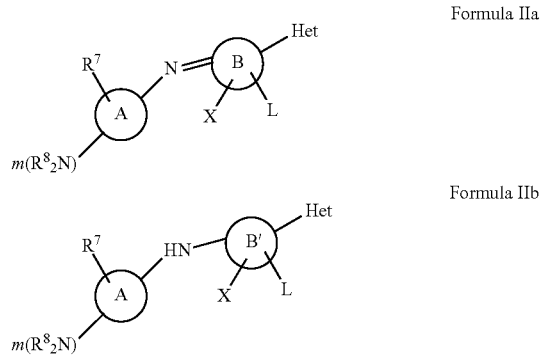

The —N═ group of Formula IIa is an imine group, also known as an azomethine or Shiff base group. The imine group is the bridge oxidatively formed between the developer moiety resulting from the developer precursor of Formula III and the auxochrome substituted developer moiety resulting from the coupler precursor of Formula I. The reduced form of the imine, an —NH— group, is the bridge between the developer moiety and the auxochrome substituted moiety of Formula IIb.

The descriptions of the groups making up Formula IIa and IIb are the same as the descriptions of Formula I, the auxochrome substituted coupler, and Formula III, the developer. Preferred embodiments of Formulas IIa and IIb include the preferred embodiments of Formula I and Formula III.

Kits

It is understood that the examples of methods of use and embodiments described herein are for illustrative purposes only and that various modifications or changes in light thereof will be suggested to one skilled in the art without departing from the scope of the present invention. Retail oxidative hair dye compositions are usually sold in kits comprising, in individually packaged components such as separate containers, a dye component (also called "dye cream" for emulsions or "dye liquid" for solutions) comprising the oxidative dye precursors and alkalizing agent which is typically ammonia in a suitable carrier and; a oxidizing component (also called "hydrogen peroxide cream" for emulsions or "hydrogen peroxide liquid" for solutions) comprising the oxidizing agent (usually hydrogen peroxide). The consumer mixes the dye component and oxidizing component together immediately before use and applies it onto the hair. Similarly, retail bleaching compositions are also usually sold as a kit comprising two or three individually packaged components typically in two or three separate containers. The first component comprises the ammonium ion source (e.g. ammonia), the second component comprises the oxidizing agent and the third (optional) component comprises a second oxidizing agent. The bleaching compositions are obtained by mixing the above-mentioned compositions immediately before use.

For, the professional hair salon market, the hair dye component and the oxidizing component and/or bleaching compositions are typically supplied independently to allow the professional to select a preferred combination.

After working the combined mixture for a few minutes (to insure uniform application to all of the hair), the oxidative dye composition is allowed to remain on the hair for an amount sufficient for the dyeing to take place (usually from about 2 to about 60 minutes, typically about 30 to about 45 minutes). The consumer or salon professional then rinses the hair thoroughly with water and/or shampoo and allows it to dry. It will be observed that the hair has changed from its original colour to the desired colour.

In both retail and professional applications, an optional conditioning agent can also be provided. In this embodiment, all three compositions can be mixed immediately before use and applied together, or the conditioning agent can be applied (after an optional rinse step), as a post-treatment immediately after the oxidative dye composition or bleaching composition resulting from the mixture of the other containers.

The kits may also comprise as optional components a pre-treatment composition and/or a colour refresher composition. Such colour refresher compositions comprise at least one pre-formed dye and may be applied to the hair immediately after the oxidative colour i.e. from about 1 minute after oxidative hair dye or bleach application to about 60 days after the application. These colour refresher compositions can be used to increase the initial colour obtained and or boost the colour during the wash and style cycle until the next oxidative colouring or bleaching event.

The auxochrome substituted coupler and developer of the foregoing embodiments of the invention can be managed as a kit for use in dying keratin fibers, preferably human hair. A kit is an aspect of the present invention because the oxidizer composition cannot be premixed with developer and coupler or with the leuco dye until just before use. To do so will result in premature production of the azomethine dye or oxidation of the leuco dye to a colored dye.

The kit for production and use of an azomethine dye includes a first composition of developer of Formula III and an auxochrome substituted coupler of Formula I in a container, jar, vessel, vial, bottle, tube or receptacle. The composition may also be formulated with optional excipients suitable for treatment of hair during a dying procedure including one or more of a conditioner, an emulsifier, an emollient, a surfactant, a preservative, an antioxidant, an antistatic agent, an anti-frizz agent, an anti-dandruff agent, a viscosity modifier, a thickener, a lubricant, a humectant, a fragrance, a diluent, and any combination thereof.

The kit for production and use of a leuco dye includes a first composition of the leuco dye described below. The leuco dye composition may also be formulated with optional excipients suitable for treatment of hair during a dying procedure including one or more of a conditioner, an emulsifier, an emollient, a surfactant, a preservative, an antioxidant, an antistatic agent, an anti-frizz agent, an anti-dandruff agent, a viscosity modifier, a thickener, a lubricant, a humectant, a fragrance, a diluent, and any combination thereof.

In each instance of a kit (azomethine or leuco dye kit), a second composition of oxidizing agent in a separate container, jar, vessel, vial, bottle, tube or receptacle is included. The oxidizer may be a peroxide, a persulfate, a perborate, a percarbonate, an alkali metal bromate, a ferricyanide, a redox enzyme with appropriate donors and cofactors or any mixture or combination thereof. The redox enzyme may be a peroxide, a persulfate, a perborate, a percarbonate, an alkali metal bromate, a ferricyanide, a redox enzyme with appropriate donors and cofactors or any mixture or combination thereof. A stabilizer may also be included to prevent excessive premature decomposition of the oxidizer.

The first and second compositions of the kit may be formulated as an aqueous lotion, creme or gel.

Methods of Manufacture

The kits described hereinabove and the compositions in each container can be manufactured utilizing any one of the standard approaches, these include a) 'Oil-in-water' process, b) 'Phase Inversion' process and c) 'One-pot' process. For example, when using "oil-in-water" process, surfactants of the present invention are added to approximately 50% of total water amount of the composition at about 90° C., homogenized for 15 to 30 min, then cooled to room temperature thus forming gel network thickener premix; this premix is then mixed cold with remaining amounts of water, other optional components and/or oxidizing agent, thus forming the first and second component parts of the above described bleaching or colouring kit.

The coloring compositions of the invention, and the corresponding oxidative precursor (developer and coupler composition and oxidizing agent composition, may be manufactured by conventional processes known in the art for manufacturing oxidative dyeing products, and ad-mixing the ingredients of each component composition in suitable vessels, followed by packaging in appropriate individual containers. The components may be for example packaged in plastic or aluminium bottles.

In particular, the present invention may be provided as a kit comprising different components to be mixed by the consumer or salon stylist to obtain a hair dyeing composition according to the invention. Such a kit may comprise a tint composition comprising and a developer composition as indicated above.

The kit may be presented in a single package comprising separate containers for the tint composition, the developer composition, and optionally a conditioner, a color refresher or other hair treatment product, instructions for use, gloves. The instructions for use include the steps of the method described above and optionally provide visual cues or pictures for the desired steps of the method. Kits are usually sold in retail products with enough material in each component for preparing a hair dyeing composition for one use.

The composition may be dispensed as a foam using for example manually-actuable, non-aerosol dispenser such as a pump or squeeze foamers, aerosol mousse. See for example EP 613,728 B1, WO 97/013585 A1, EP 1,716,933A1, U.S. Pat. Nos. 3,709,437, 3,937,364, 4,022,351, 4,147,306, 4,184,615, 4,615,467 and FR 2,604,622. One particular example of a squeeze foamer useful herein is able to dispense from an upright or inverted position such as the one discussed in U.S. Pat. No. 6,604,693 assigned to Taplast, and more specifically, at column 2, line 65, through column 4, line 67 of that patent.

The composition may also be dispensed as a solid form to which water is added to generate the oxidant and form a thickened vehicle suitable for hair coloring.

Packaging and Dispensing Devices

The present invention may be provided in a variety of packaging devices and/or dispensing devices. These dispensing devices can come in the form of separate devices which may be used independently or in combination with one another. Typically, the hair colouring or bleaching compositions are contained within separate single or multi compartment containers so that the compositions can be stored separately from one another before use. The compositions are then mixed together by a mixing means and then dispensed from the device and applied to the consumer's hair by an application means.

The most common packaging device which can be used for the present invention involves storing the developer in a container such as a bottle, tube, aerosol, or a sachet and separately storing the dye lotion in an additional compartment within the developer container or more preferably in a separate container which may be identical such as a dual sachet or aerosol systems for example or different such as a bottle and tube system. Any combination may be used and is typically contingent on the type of composition being stored i.e. whether or not it is a thick or thin type. The consumer or hair salon professional may mix the oxidizing component and the dye component by any means. This may simply involve the use of a mixing bowl into which the compositions are dispensed and then mixed, preferably using a mixing means such as a tool. Alternatively, it may involve the addition of one of the compositions into the container of the other composition (typically the dye composition is added to the oxidizing composition), followed by manual shaking or mixing with a tool. Another system involves the perforation or displacement of a seal located between the separate compartments of the dye and oxidizing composition within a single container or sachet followed by manual mixing within the container or in a separate and or additional container.

The devices described herein above can also be used in combination with a product delivery and or application tool to aid application of the product onto the hair. These devices may be of a very simple nature such as a nozzle attached to one of the containers or a separate applicator device such as a comb or brush. Such combs and brushes can be adapted in order to achieve particular effects, whether it may be quick and even coverage or root/hairline touch up, or highlights or streaks. Alternatively, the container or one of the containers may be provided with a comb attached to or instead of the dispensing nozzle whereby the product is dispensed through hollow tines and dispensing apertures located in the comb tines. The comb tines may be provided with single or multiple openings along the tines to improve product application and evenness especially root to tip. Product dispensation can be achieved by mechanical pressure applied to the container for example delaminating bottles or any of the mechanisms described hereinabove. The comb may be provided on the container such as to facilitate easy application and may be positioned vertically (so called verticomb) or at an angle to allow the consumer to access all areas. All devices may be designed to have inter-changeability, so that a range of different tools for hair application can be provided to the consumer.

The application devices may also include devices which assist in achieving particular effects such as highlighting such as highlighting combs, brushes and tools, foils and highlighting caps. Highlighting devices comprising a hinged device into which an amount of composition is placed and then used to apply the composition to pre-determined/selected hair strands may also be used.

Foam

Alternatively, the compositions of the invention may be provided in the form of foam which is applied to the hair. Foam formation is typically achieved by the use of a foaming agent incorporated within the mixed composition (typically present in either the oxidizing composition or the dye composition or both) in combination with a manually operated foaming device. Such manually operated foaming devices are known in the art and include aerosols devices, squeeze foamers and pump foamers.

Suitable foaming agents includes surfactants such as anionic, nonionic and amphoteric surfactants, nonionic surfactants being preferred; polysaccharides (as described herein); polyvinyl pyrrolidone and copolymers thereof; acrylic polymers such as Acrylates copolymer (Aculyn 33) and Acrylates/Steareth-20 methacrylates (Aculyn 22); C12-C24 fatty acids such as stearates and mixtures thereof.

Methods of Use

The hair coloring compositional embodiments of the present invention may be obtained by mixing immediately prior to use the developer/auxochrome substituted coupler composition and an oxidizer composition. A sufficient amount of the mixture is applied to the hair, according to the hair abundance, generally from about 60 to about 250 grams. Upon such preparation, the composition is applied to the hair to be dyed and remains in contact with the hair for an amount of time effective to dye the hair. Typically, the hair dye composition is allowed to act on the hair from about 2 to about 60, preferably about 15 to about 45, more preferably about 30 minutes, at a temperature ranging from 15° C. to about 50° C. Thereafter, the hair is rinsed with water to remove the composition and dried. If necessary, the hair is washed with a shampoo and rinsed, e.g., with water or a weakly acidic solution, such as a citric acid or tartaric acid solution, and dried. Optionally, a separate conditioning product may also be provided.

The method of treating hair with the composition may therefore include the steps of:
(i) providing a tint composition comprising the gel network thickening system and if present an alkalizing agent and oxidative precursor dyes and/or direct dyes;
(ii) providing a developer composition comprising an oxidizing agent;
(iii) mixing the developer (oxidizer) composition with the dye composition to obtain a hair coloring composition according to the invention.
(iv) applying the composition for the oxidative dyeing of keratin fibers onto the hair.
The glycerol can be comprised in the dye composition or the developer composition or distributed in both components. Typically glycerol will be at least comprised in the dye composition to serve as solvent for the dyes.

The method may further include waiting a period of time, typically between 2 minutes and 60 minutes, and then rinsing the hair coloring composition from the hair. The hair coloring composition can be applied on hair via applicator bottle or brush. It can be used on full head or partly on single strands (highlight application) as common highlight applicator foils, caps and special applicators can be used, but also freehand techniques such as balayage, with brush and/or combs can be possible. The composition can also be applied as a mousse via a manual spray, a pressurized container or an aerosol mousse. The composition may be dispensed as a solid form to which water is added to generate the oxidant and form a thickened vehicle suitable for hair coloring.

After working the combined mixture of oxidizable dye precursors (developer and coupler) and oxidizing agent for a few minutes (to insure uniform application to all of the hair), the oxidative dye composition is allowed to remain on the hair for an amount sufficient for the dyeing to take place (usually from about 2 to about 60 minutes, typically about 30 to about 45 minutes). The consumer or salon professional then rinses the hair thoroughly with water and/or shampoo and allows it to dry. It will be observed that the hair has changed from its original colour to the desired colour.

In both retail and professional applications, an optional conditioning agent can also be provided. In this embodiment, all three compositions can be mixed immediately before use and applied together, or the conditioning agent can be applied (after an optional rinse step), as a post-treatment immediately after the oxidative dye composition or bleaching composition resulting from the mixture of the other containers.

According to these aspects of the invention the method of dying keratin fibers involves use of an azomethine dye or leuco dye embodiment of the invention. For an azomethine dye, the contents of the azomethine kit are combined in situ as described above just before use. The keratin fibers can optionally be washed with surfactant and/or shampoo, rinsed and dried to dampness before applying the azomethine dye. Additionally, the keratin fibers can be bleached prior to or subsequent to washing and following bleaching, the keratin fibers can be rinsed and dried to dampness before the azomethine dye is applied.

The method aspect of the invention concerning the leuco dye is practiced in a similar way to the practice of the method concerning the azomethine dye. However, the composition containing the leuco dye is applied first to the keratin fibers and subsequently the oxidizer composition is applied to the fibers to conver the leuco dye to a colored compound. Washing and bleaching steps can be practiced in the same way as described for the azomethine dye method.

Additional Excipients and Ingredients

The embodiments of the auxochrome substituted coupler of Formula I, the developer of Formula III, the kits and the azomethine and leuco dye of Formula IIa and IIb according to the present invention may include, in addition to the ingredients indicated above, further ingredients in order to further enhance the properties of the composition, as long as these are not excluded by the claims.

Suitable further ingredients include, but not limited to: solvents; oxidizing agents; alkalizing agents; oxidative dye precursors, direct dyes; chelants; radical scavengers; pH modifiers and buffering agents; thickeners and/or rheology modifiers; carbonate ion sources; peroxymonocarbonate ion sources; anionic, cationic, nonionic, amphoteric or zwitterionic surfactants, and mixtures thereof; anionic, cationic, nonionic, amphoteric or zwitterionic polymers, and mixtures thereof; fragrances; enzymes; dispersing agents; peroxide stabilizing agents; antioxidants; natural ingredients (such as proteins, protein compounds, and plant extracts); conditioning agents (such as silicones and cationic polymers); ceramides; preserving agents; opacifiers and pearling agents (such as titanium dioxide and mica); and mixtures thereof. Suitable further ingredients referred to above, but not specifically described below, are listed in the International Cosmetics Ingredient Dictionary and Handbook, (8th ed.; The Cosmetics, Toiletry, and Fragrance Association). Particularly, vol. 2, sections 3 (Chemical Classes) and 4 (Functions), which are useful in identifying specific adjuvants to achieve a particular purpose or multipurpose. A few of these ingredients are discussed hereinbelow, whose disclosure is of course non-exhaustive.

Solvents

The embodiments of the auxochrome substituted coupler of Formula I, the developer of Formula III, the kits and the azomethine and leuco dye of Formula IIa and IIb according to the present invention may include a solvent. The solvent may be selected from water, or a mixture of water and at least one organic solvent to dissolve the compounds that would not typically be sufficiently soluble in water.

Suitable organic solvents include, but are not limited to: C1 to C4 lower alkanols (such as ethanol, propanol, isopropanol); aromatic alcohols (such as benzyl alcohol and phenoxyethanol); polyols and polyol ethers (such as carbitols, 2-butoxyethanol, propylene glycol, propylene glycol monomethyl ether, diethylene glycol monoethyl ether, monomethyl ether, hexylene glycol, glycerol, ethoxy glycol, butoxydiglycol, ethoxydiglycerol, dipropyleneglocol, polygylcerol); propylene carbonate; and mixtures thereof.

In one embodiment, the solvent may be selected from the group consisting of water, ethanol, propanol, isopropanol, glycerol, 1,2-propylene glycol, hexylene glycol, ethoxy diglycol, and mixtures thereof.

Typically, the composition may comprise water as a main ingredient, particularly in a total amount ranging from at least about 50%, alternatively from at least about 60%, alternatively from at least about 70%, by weight of the total composition. Typically, when present, the composition comprises a total amount of organic solvents ranging from about 1% to about 30/o, by weight of the total composition.

Oxidizing Agents

The kit embodiments according to the present invention may include at least one source of an oxidizing agent. Any oxidizing agent known in the art may be used. Preferred oxidizing agents are water-soluble peroxygen oxidizing agents. As used herein, "water-soluble" means that in standard conditions at least about 0.1 g, preferably about 1 g, more preferably about 10 g of the oxidizing agent can be dissolved in 1 liter of deionized water at 25° C. The oxidizing agents are valuable for the initial solubilisation and decolorisation of the melanin (bleaching) and accelerate the oxidation of the oxidative dye precursors (oxidative dyeing) in the hair shaft.

Typically, the composition may comprise a total amount of oxidizing agents ranging from about 0.1% to about 10%, alternatively from about 1% to about 7%, alternatively from about 2% to about 5%, by weight of the total composition.

Suitable water-soluble oxidizing agents include, but are not limited to: inorganic peroxygen materials capable of yielding hydrogen peroxide in an aqueous solution.

Suitable water-soluble peroxygen oxidizing agents include, but are not limited to: hydrogen peroxide; inorganic alkali metal peroxides (such as sodium periodate and sodium peroxide); organic peroxides (such as urea peroxide and melamine peroxide); inorganic perhydrate salt bleaching compounds (such as the alkali metal salts of perborates, percarbonates, perphosphates, persilicates, persulphates and the like); and mixtures thereof. Inorganic perhydrate salts may be incorporated for example as monohydrates, tetrahydrates. Alkyl/aryl peroxides and/or peroxidases may also be used. Mixtures of two or more such oxidizing agents can be used if desired. The oxidizing agents may be provided in aqueous solution or as a powder which is dissolved prior to use.

In a specific embodiment, the composition comprises a water-soluble oxidizing agent selected from the group consisting of hydrogen peroxide, percarbonates (which may be used to provide a source of both oxidizing agent and carbonate ions and or ammonium ions), persulphates, and mixtures thereof.

The oxidizing composition forming the second composition of the kit embodiments of the present invention may be based on any desired formulation chassis, including any commercial product, for example an oil-in-water emulsion. Typical oxidizing compositions comprise about 6% or about 9% of the H2O2 relative to the total weight of the developer composition. A commercial example is the Welloxon® Emulsion with respectively about 6% and about 9% H2O2, marketed by Wella and comprising as INCI ingredients: Water, H2O2, Cetearyl Alcohol, Ceteareth-25, Salicylic Acid, Phosphoric Acid, Disodium Phosphate, Etidronic Acid.

Alkalizing Agents

The first composition of the kit embodiments according to the present invention may further include an alkalizing agent. Any alkalizing agent known in the art may be used. Typically, the composition may comprise an amount of alkalizing agents ranging from about 0.1% to about 10%, alternatively from about 0.5% to about 6%, alternatively from about 1% to about 4%, by weight of the total composition.

Suitable alkalizing agents include, but are not limited to: ammonia; alkanolamines (such as monoethanolamine, diethanolamine, triethanolamine, monopropanolamine, dipropanolamine, tripropanolamine 2-amino-2-methyl-1,3-propanediol, 2-amino-2-methyl-1-propanol, and 2-amino-2-hydroxymethyl-1,3-propanediol); guanidium salts; alkali metal and ammonium hydroxides (such as sodium hydroxide); alkali metal and ammonium carbonates; and mixtures thereof. Typical alkalizing agents are ammonia and/or monoethanolamine. Preferably, if present, the ammonium ions and carbonate ions are present in the composition at a weight ratio of from 3:1 to 1:10, alternatively from 2:1 to 1:5.

Oxidative Dye Precursor Concentrations (Developers and Couplers)

The compositional embodiments according to the present invention as described above include embodiments of oxidative dye precursors, which include the auxochrome substituted coupler embodiments of Formula I and the developer embodiments of Formula III. Developers are also generally known as primary intermediates and the couplers are also generally known as secondary intermediates.

Typically, the embodiments of the invention may include a total amount of oxidative dye precursors (both of the developer and auxochrome embodiments of Formulas III and I) ranging up to about 12%, alternatively from about 0.1% to about 10%, alternatively from about 0.3% to about 8%, alternatively from about 0.5% to about 6%, by weight of the total composition.

Typical molar ratios of developer to coupler will range from about 1:1 to about 2:1, preferably about 1:1.

Direct Dyes

The compositional embodiments according to the present invention may further comprise compatible direct dyes, in an amount sufficient to provide additional coloring, particularly with regard to intensity. Typically, the composition may comprise a total amount of direct dyes ranging from about 0.05% to about 4%, by weight of the total composition.

Suitable direct dyes include but are not limited to: Acid dyes such as Acid Yellow 1, Acid Orange 3, Acid Black 1, Acid Black 52, Acid Orange 7, Acid Red 33, Acid Yellow 23, Acid Blue 9, Acid Violet 43, HC Blue 16, Acid Blue 62, Acid Blue 25, Acid Red 4; Basic Dyes such as Basic Brown 17, Basic Red 118, Basic Orange 69, Basic Red 76, Basic Brown 16, Basic Yellow 57, Basic Violet 14, Basic Blue 7, Basic Blue 26, Basic Red 2, Basic Blue 99, Basic Yellow 29, Basic Red 51, Basic Orange 31, Basic Yellow 87, Basic Blue 124, 4-(3-(4-amino-9,10-dioxo-9,10-dihydroanthracen-1-ylamino)propyl)-4-methylmorpholin-4-ium-methylsulfate, (E)-1-(2-(4-(4,5-dimethylthiazol-2-yl)diazenyl)phenyl) (ethyl)amino)ethyl)-3-methyl-1H-imidazol-3-ium chloride, (E)-4-(2-(4-(dimethylamino)phenyl)diazenyl)-1-methyl-1H-imidazol-3-ium-3-yl)butane-1-sulfonate, (E)-4-(4-(2-methyl-2-phenylhydrazono)methyl)pyridinium-1-yl)butane-1-sulfonate, N,N-dimethyl-3-(4-(methylamino)-9,10-dioxo-4a,9,9a,10-tetrahydroanthracen-1-ylamino)-N-propylpropan-1-aminium bromide; Disperse Dyes such as Disperse Red 17, Disperse Violet 1, Disperse Red 15, Disperse Black 9, Disperse Blue 3, Disperse Blue 23, Disperse Blue 377; Nitro Dyes such as 1-(2-(4-nitrophenylamino)ethyl)urea, 2-(4-methyl-2-nitrophenylamino)ethanol, 4-nitrobenzene-1,2-diamine, 2-nitrobenzene-1,4-diamine, Picramic acid, HC Red No. 13, 2,2'-(2-nitro-1,4-phenylene)bis(azanediyl)diethanol, HC Yellow No. 5, HC Red No. 7, HC Blue No. 2, HC Yellow No. 4, HC Yellow No. 2, HC Orange No. 1, HC Red No. 1, 2-(4-amino-2-chloro-5-nitrophenylamino)ethanol, HC Red No. 3, 4-amino-3-nitrophenol, 4-(2-hydroxyethylamino)-3-nitrophenol, 2-amino-3-nitrophenol, 2-(3-(methylamino)-4-nitrophenoxy)ethanol, 3-(3-amino-4-nitrophenyl)propane-1,2-diol, HC Yellow No. 11, HC Violet No. 1, HC Orange No. 2, HC Orange No. 3, HC Yellow No. 9, HC Red No. 10, HC Red No. 11, 2-(2-hydroxyethylamino)-4,6-dinitrophenol, HC Blue No. 12, HC Yellow No. 6, HC Yellow No. 12, HC Blue No. 10, HC Yellow No. 7, HC Yellow No. 10, HC Blue No. 9, 2-chloro-6-(ethylamino)-4-nitrophenol, 6-nitropyridine-2,5-diamine, HC Violet No. 2, 2-amino-6-chloro-4-nitrophenol, 4-(3-hydroxypropylamino)-3-nitrophenol, HC Yellow No. 13, 6-nitro-1,2,3,4-tetrahydroquinoxaline, HC Red No. 14, HC Yellow No. 15, HC Yellow No. 14, N2-methyl-6-nitropyridine-2,5-diamine, N1-allyl-2-nitrobenzene-1,4-diamine, HC Red No. 8, HC Green No. 1, HC Blue No. 14; Natural dyes such as Annato, Anthocyanin, Beetroot, Carotene, Capsanthin, Lycopene, Chlorophyll, Henna, Indigo, Cochineal; and mixtures thereof.

Chelants

The compositional embodiments according to the present invention may further include chelants (also known as "chelating agent", "sequestering agent", or "sequestrant") in an amount sufficient to reduce the amount of metals available to interact with formulation components, particularly oxidizing agents, more particularly peroxides. Chelants are well known in the art and a non-exhaustive list thereof can be found in A E Martell & R M Smith, Critical Stability Constants, Vol. 1, Plenum Press, New York & London (1974) and A E Martell & R D Hancock, Metal Complexes in Aqueous Solution, Plenum Press, New York & London (1996), both incorporated herein by reference.

Typically, the compositional embodiments may include a total amount of chelants ranging from at least about 0.01%, alternatively from about 0.01% to about 5%, alternatively from about 0.25% to about 3%, alternatively from about 0.5% to about 1%, by weight of the total composition.

Suitable chelants include, but are not limited to: carboxylic acids (such as aminocarboxylic acids), phosphonic acids (such as aminophosphonic acids), polyphosphoric acids (such as linear polyphosphoric acids), their salts thereof, and mixtures thereof. By "salts thereof", it is meant—in the context of chelants—all salts comprising the same functional structure as the chelant they are referring to and including alkali metal salts, alkaline earth salts, ammonium salts, substituted ammonium salts, and mixtures thereof; alternatively sodium salts, potassium salts, ammonium salts, and mixtures thereof, alternatively monoethanolammonium salts, diethanolammonium salts, triethanolammonium salts, and mixtures thereof.

Suitable aminocarboxylic acid chelants comprise at least one carboxylic acid moiety (—COOH) and at least one nitrogen atom. Suitable aminocarboxylic acid chelants include, but are not limited to: diethylenetriamine pentaacetic acid (DTPA), ethylenediamine disuccinic acid (EDDS), ethylenediamine diglutaric acid (EDGA), 2-hydroxypropylenediamine disuccinic acid (HPDS), glycinamide-N,N'-disuccinic acid (GADS), ethylenediamine-N—N'-diglutaric acid (EDDG), 2-hydroxypropylenediamine-N—N'-disuccinic acid (HPDDS), ethylenediaminetetraacetic acid (EDTA), ethylenedicysteic acid (EDC), ethylenediamine-N—N'-bis(ortho-hydroxyphenyl acetic acid) (EDDHA), diaminoalkyldi(sulfosuccinic acids) (DDS), N,N'-bis(2-hydroxybenzyl)ethylenediamine-N,N'-diacetic acid (HBED), their salts thereof, and mixtures thereof.

Other suitable aminocarboxylic type chelants include, but are not limited to: iminodiacetic acid derivatives such as N-2-hydroxyethyl N,N diacetic acid or glyceryl imino diacetic acid, iminodiacetic acid-N-2-hydroxypropyl sulfonic acid and aspartic acid N-carboxymethyl N-2-hydroxypropyl-3-sulfonic acid, β-alanine-N,N'-diacetic acid, aspartic acid-N,N'-diacetic acid, aspartic acid-N-monoacetic acid and iminodisuccinic acid chelants, ethanoldiglycine acid, their salts thereof, their derivatives thereof, and mixtures thereof. Further suitable aminocarboxylic type chelants include, but are not limited to: dipicolinic acid, 2-phosphonobutane-1,2,4-tricarboxylic acid, their salts thereof, their derivatives thereof, and mixtures thereof.

Suitable aminophosphonic acid chelants comprise an aminophosphonic acid moiety (—$PO_3H_2$) or its derivative —$PO_3R_2$, wherein $R_2$ is a $C_1$ to $C_6$ alkyl or aryl radical and salts thereof. Suitable aminophosphonic acid chelants include, but are not limited to: aminotri-(1-ethylphosphonic acid), ethylene-diaminetetra-(1-ethylphosphonic acid), aminotri-(1-propylphosphonic acid), aminotri-(isopropylphosphonic acid), their salts thereof, and mixtures thereof; alternatively aminotri-(methylenephosphonic acid), ethylenediamine-tetra-(methylenephosphonic acid) (EDTMP) and diethylene-triamine-penta-(methylenephosphonic acid) (DTPMP), their salts thereof, their derivatives thereof, and mixtures thereof.

Suitable alternative chelants include, but are not limited to: polyethyleneimines, polyphosphoric acid chelants, etidronic acid, methylglycine diacetic acid, N-(2-hydroxyethyl)iminodiacetic acid, minodisuccinnic acid, N,N-Dicarboxymethyl-L-glutamic acid, N-lauroyl-N,N',N''-ethylenediamine diacetic acid, their salts thereof, their derivatives thereof, and mixtures thereof.

In a specific embodiment, the composition comprises a chelant selected from the group consisting of diethylenetriamine-N,N',N''-polyacids, diethylenetriaminepentaacetic acid (DTPA), diethylenetriaminepenta(methylene phosphonic acid) (DTPMP), diamine-N,N'-dipolyacid, monoamine monoamide-N,N'-dipolyacid, ethylenediaminedisuccinic acid (EDDS), their salts thereof, their derivatives thereof, and mixtures thereof; alternatively ethylenediaminedisuccinic acid (EDDS).

When the composition of the invention is obtained by mixing a tint composition and a developer composition, the chelants may be incorporated in the tint composition and/or in the developer composition. A chelant is usually present in the developer composition for stability reason.

Radical Scavengers

The compositional embodiments according to the present invention may further comprise a radical scavenger. As used herein the term "radical scavenger" refers to a species that can react with a radical, preferably a carbonate radical to convert the radical species by a series of fast reactions to a less reactive species. In one embodiment, the radical scavenger is different from the alkalising agent and/or is present in an amount sufficient to reduce the damage to the hair during the colouring/bleaching process.

Typically, the compositional embodiments may comprise a total amount of radical scavengers ranging from about 0.1% to about 10%, alternatively from about 1% by weight to about 7%, by weight of the total composition.

Suitable radical scavengers include, but are not limited to: alkanolamines, amino sugars, amino acids, esters of amino acids, and mixtures thereof; alternatively 3-amino-1-propanol, 4-amino-1-butanol, 5-amino-1-pentanol, 1-amino-2-propanol, 1-amino-2-butanol, 1-amino-2-pentanol, 1-amino-3-pentanol, 1-amino-4-pentanol, 3-amino-2-methylpropan-1-ol, 1-amino-2-methylpropan-2-ol, 3-aminopropane-1,2-diol, glucosamine, N-acetylglucosamine, glycine, arginine, lysine, proline, glutamine, histidine, sarcosine, serine, glutamic acid, tryptophan, their salts thereof, and mixtures thereof; alternatively glycine, sarcosine, lysine, serine, 2 methoxyethylamine, glucosamine, glutamic acid, morpholine, piperdine, ethylamine, 3 amino-1-propanol, and mixtures thereof. As used herein, the term "salts thereof"—in the context of radical scavengers—means particularly potassium salts, sodium salts, ammonium salts, and mixtures thereof.

pH Modifiers and Buffering Agents

The compositional embodiments according to the present invention may further comprise, in addition to the alkalizing agent discussed above, a pH modifier and/or buffering agent in an amount that is sufficiently effective to adjust the pH of the composition to fall within a range from about 3 to about 13, alternatively from about 8 to about 12, alternatively from about 9 to about 11.

Suitable pH modifiers and/or buffering agents include, but are not limited to: ammonia; alkanolamides (such as monoethanolamine, diethanolamine, triethanolamine, monopropanolamine, dipropanolamine, tripropanolamine, tripropanolamine, 2-amino-2-methyl-1-propanol, 2-amino-2-hydroxymethyl-1,3,-propandiol); guanidium salts; alkali metal and ammonium hydroxides and carbonates; and mixtures thereof.

Further pH modifiers and/or buffering agents include, but are not limited to: sodium hydroxide; ammonium carbonate; acidulents (such as inorganic and inorganic acids including for example phosphoric acid, acetic acid, ascorbic acid, citric acid or tartaric acid, hydrochloric acid); and mixtures thereof.

Thickeners and/or Rheology Modifiers

The compositional embodiments according to the invention may further include a thickener in an amount sufficient to provide the composition with a viscosity so that it can be readily applied to the hair without unduly dripping off the hair and causing mess.

Typically, the composition may comprise a total amount of thickeners ranging from at least about 0.1%, alternatively at least about 0.5%, alternatively at least about 1%, by weight of the total composition.

Suitable thickeners include, but are not limited to: associative polymers, polysaccharides, non-associative polycarboxylic polymers, and mixtures thereof.

As used herein, the expression "associative polymers" means amphiphilic polymers comprising both hydrophilic units and hydrophobic units, for example, at least one C8 to C30 fatty chain and at least one hydrophilic unit. Associative polymers are capable of reversibly combining with each other or with other molecules.

Suitable associative thickeners include, but are not limited to: nonionic amphiphilic polymers comprising at least one hydrophilic unit and at least one fatty-chain unit; anionic amphiphilic polymers comprising at least one hydrophilic unit and at least one fatty-chain unit; cationic amphiphilic polymers comprising at least one hydrophilic unit and at least one fatty-chain unit; and amphoteric amphiphilic polymers comprising at least one hydrophilic unit and at least one fatty-chain unit, and mixtures thereof.

Suitable nonionic amphiphilic polymers comprising at least one fatty chain and at least one hydrophilic unit include, but are not limited to: celluloses modified with groups comprising at least one fatty chain (such as hydroxyethylcelluloses modified with groups comprising at least one fatty chain chosen from alkyl, alkenyl and alkylaryl groups); hydroxypropyl guars modified with groups comprising at least one fatty chain; polyether urethanes comprising at least one fatty chain (such as C8-C30 alkyl or alkenyl groups); copolymers of vinylpyrrolidone and of fatty-chain hydrophobic monomers; copolymers of C1-C6 alkyl acrylates or methacrylates and of amphiphilic monomers comprising at least one fatty chain; copolymers of hydrophilic acrylates or methacrylates and of hydrophobic monomers comprising at least one fatty chain, and mixtures thereof.

Suitable nonionic amphiphilic polymers comprising at least one hydrophilic unit and at least one fatty-chain unit include, but are not limited to: those polymers comprising at least one fatty-chain allyl ether unit and at least one hydrophilic unit comprising an ethylenic unsaturated anionic monomeric unit (such as a vinylcarboxylic acid unit, particularly a unit chosen from units derived from acrylic acids, methacrylic acids, and mixtures thereof), wherein the fatty-chain allyl ether unit corresponds to the monomer of formula (I) below $$CH_2=C(R1)CH_2OB_nR \quad (I)$$

in which R1 is chosen from H and CH3, B is an ethyleneoxy radical, n is chosen from zero and integers ranging from 1 to 100, R is chosen from hydrocarbon-based radicals chosen from alkyl, alkenyl, arylalkyl, aryl, alkylaryl and cycloalkyl radicals, comprising from 8 to 30 carbon atoms, and, further, for example, from 10 to 24 carbon atoms and even further, for example, from 12 to 18 carbon atoms.

Suitable anionic amphiphilic polymers include, but are not limited to: those polymers comprising at least one hydrophilic unit of unsaturated olefinic carboxylic acid type, and at least one hydrophobic unit of the type such as a (C8-C30) alkyl ester or (C8-C30) oxyethylenated alkyl ester of an unsaturated carboxylic acid, wherein the hydrophilic unit of unsaturated olefinic carboxylic acid type corresponds to, for example, the monomer of formula (II) below $$CH_2=C(R1)COOH \quad (II)$$

in which R1 is chosen from H, CH3, C2H5 and CH2COOH (i.e. acrylic acid, methacrylic, ethacrylic and itaconic acid units); and wherein the hydrophobic unit of the type such as a (C8-C30) alkyl ester or (C8-C30) oxyethylenated alkyl ester of an unsaturated carboxylic acid corresponds to, for example, the monomer of formula (III) below $$CH_2=C(R1)COOB_nR2 \quad (III)$$

in which R1 is chosen from H, CH3, C2H5 and CH2COOH (i.e. acrylate, methacrylate, ethacrylate and itaconate units), B is an ethyleneoxy radical, n is chosen from zero and integers ranging from 1 to 100, R2 is chosen from C8-C30 alkyl radicals, for example, C12-C22 alkyl radical. Anionic amphiphilic polymers may further be cross-linked. The crosslinking agent can be a monomer comprising a group (IV) below $$CH_2=C< \quad (IV)$$

with at least one other polymerizable group whose unsaturated bonds are not conjugated with respect to one another. Mention may be made, for example, of polyallyl ethers such as polyallylsucrose and polyallyl pentaerythritol.

Suitable cationic amphiphilic polymers include, but are not limited to: quaternized cellulose derivatives and polyacrylates comprising amino side groups. The quaternized cellulose derivatives are, for example, chosen from quaternized celluloses modified with groups comprising at least one fatty chain, such as alkyl, arylalkyl and alkylaryl groups comprising at least 8 carbon atoms, and mixtures thereof, quaternized hydroxyethylcelluloses modified with groups comprising at least one fatty chain, such as alkyl, arylalkyl and alkylaryl groups comprising at least 8 carbon atoms, and mixtures thereof. The alkyl radicals borne by the above quaternized celluloses and hydroxyethylcelluloses, for example, contain from 8 to 30 carbon atoms. The aryl radicals, for example, are chosen from phenyl, benzyl, naphthyl and anthryl groups.

Suitable amphoteric amphiphilic polymers comprising at least one hydrophilic unit and at least one fatty-chain unit, may be made, for example, of methacrylamidopropyltrimethylammonium chloride/acrylic acid/C8-C30 alkyl methacrylate copolymers, wherein the alkyl radical is, for example, a stearyl radical.

Preferred associative polymers comprise at least one hydrophilic unit which is unsaturated carboxylic acid or its derivatives, and at least one hydrophobic unit which is a C8 to C30 alkyl ester or oxyethylenated C8-C30 alkyl ester of unsaturated carboxylic acid. The unsaturated carboxylic acid is preferably acrylic acid, methacrylic acid or itaconic acid. Commercially available materials include those sold as Aculy-22 by Rohm & Haas; Permulen TR1, Carbopol 2020, Carbopol Ultrez-21 by Noveon, Structure 2001/3001 by National Starch.

Other preferred associative polymers include polyether polyurethane, commercially available as Aculyn-44/-46 by Rohm and Haas. Further preferred associative polymers include cellulose modified with groups comprising at least one C8-C30 fatty chain, commercially available under the trade name Natrosol Plus Grade 330 CS by Aqualon.

Suitable non-associative cross-linked polycarboxylic polymers include, but are not limited to: cross-linked acrylic acid homopolymers, copolymers of acrylic or (meth)acrylic acid and of C1-C6 alkyl acrylate or (meth)acrylate, and mixtures thereof. Commercially available materials include those sold as Carbopol 980/981/954/2984/5984 by Noveon, Synthalen M/Synthalen L/Synthalen K by 3V Sigma, Aculyn-33 by Rohm and Haas.

Suitable polysaccharides include, but are not limited to: glucans, modified and unmodified starches (such as those derived, for example, from cereals, for instance wheat, corn or rice, from vegetables, for instance yellow pea, and tubers, for instance potato or cassava), amylose, amylopectin, glycogen, dextrans, celluloses and derivatives thereof (methylcelluloses, hydroxyalkylcelluloses, ethyl hydroxyethylcelluloses, and carboxymethylcelluloses), mannans, xylans, lignins, arabans, galactans, galacturonans, chitin, chitosans, glucuronoxylans, arabinoxylans, xyloglucans, glucomannans, pectic acids and pectins, alginic acid and alginates, arabinogalactans, carrageenans, agars, glycosaminoglucans, gum arabics, gum tragacanths, ghatti gums, karaya gums, carob gums, galactomannans, such as guar gums, and nonionic derivatives thereof (hydroxypropyl guar) and biopolysaccharides, such as xanthan gums, gellan gums, welan gums, scleroglucans, succinoglycans, and mixtures thereof. Suitable polysaccharides are described in "Encyclopedia of Chemical Technology", Kirk-Othmer, Third Edition, 1982, volume 3, pp. 896-900, and volume 15, pp. 439-458, in "Polymers in Nature" by E. A. MacGregor and C. T. Greenwood, published by John Wiley & Sons, Chapter 6, pp. 240-328,1980, and in "Industrial Gums-Polysaccharides and their Derivatives", edited by Roy L. Whistler, Second Edition, published by Academic Press Inc., all three being incorporated herein by reference.

A preferred polysaccharide is a bio-polysaccharide, particularly bio-polysaccharides selected from xanthan gum, gellan gum, welan gum, scleroglucan or succinoglycan; commercially available as Keltrol® T by Kelco and Rheozan® by Rhodia Chimie. Another preferred polysaccharide is hydroxypropyl starch derivative, particularly hydroxypropyl starch phosphate, commercially available as Structure XL® by National Starch.

Commercially available salt-tolerant thickeners include, but not limited to: xanthan, guar, hydroxypropyl guar, scleroglucan, methyl cellulose, ethyl cellulose (commercially available as Aquacote), hydroxyethyl cellulose (Natrosol), carboxymethyl cellulose, hydroxypropylmethyl cellulose, microcrystalline cellulose, hydroxybutylmethyl cellulose, hydroxypropyl cellulose (Klucel), hydroxyethyl ethyl cellulose, cetyl hydroxyethyl cellulose (Natrosol Plus 330), N-vinylpyrollidone (Povidone), Acrylates/Ceteth-20 Itaconate Copolymer (Structure 3001), hydroxypropyl starch phosphate (Structure ZEA), polyethoxylated urethanes or polycarbamyl polyglycol ester such as PEG-150/Decyl/SMDI copolymer (Aculyn 44), PEG-150/Stearyl/SMDI copolymer (Aculyn 46), trihydroxystearin (Thixcin), acrylates copolymer (Aculyn 33) or hydrophobically modified acrylate copolymers (such as Acrylates/Steareth-20 Methacrylate Copolymer as Aculyn 22), acrylates/steareth-20 methacrylate crosspolymer (Aculyn 88), acrylates/vinyl neodecanoate crosspolymer (Aculyn 38), acrylates/beheneth-25 methacrylate copolymer (Aculyn 28), acrylates/C10-30 alkyl acrylate crosspolymer (Carbopol ETD 2020), non-ionic amphophilic polymers comprising at least one fatty chain and at least one hydrophilic unit selected from polyether urethanes comprising at least one fatty chain, blends of Ceteth-10 phosphate, Di-cetyl phosphate and Cetearyl alcohol (available as Crodafos CES), and mixtures thereof.

Carbonate Ion Sources

The compositional embodiments according to the present invention may further include a source of carbonate ions, carbamate ions, hydrogen carbonate ions, and mixtures thereof in a sufficient amount to reduce damage to the hair during the coloring process.

Typically, the composition may comprise a total amount of a carbonate ion source ranging from about 0.1% to about 15%, alternatively from about 0.1% to about 10%, alternatively from about 1% to about 7%, by weight of the total composition.

Suitable carbonate ion sources include, but are not limited to: sodium carbonate, sodium hydrogen carbonate, potassium carbonate, potassium hydrogen carbonate, guanidine carbonate, guanidine hydrogen carbonate, lithium carbonate, calcium carbonate, magnesium carbonate, barium carbonate, ammonium carbonate, ammonium hydrogen carbonate and mixtures thereof; alternatively sodium hydrogen carbonate, potassium hydrogen carbonate, and mixtures thereof, alternatively ammonium carbonate, ammonium hydrogen carbonate, and mixtures thereof.

Conditioning Agents

The compositional embodiments according to the present invention may further comprise a conditioning agent, and/or be used in combination with a composition comprising a conditioning agent.

Typically, the composition may comprise a total amount of conditioning agents ranging from about 0.05% to about 20%, alternatively from about 0.1% to about 15%, alternatively from about 0.2% to about 10%, alternatively from about 0.2% to about 2%, alternatively from about 0.5% to 2%, by weight of the total composition. The conditioning agent may be included in a separate pre- and/or post-treatment composition.

Suitable conditioning agents include, but are not limited to: silicones, aminosilicones, fatty alcohols, polymeric resins, polyol carboxylic acid esters, cationic polymers, cationic surfactants, insoluble oils and oil derived materials and mixtures thereof. Additional conditioning agents include mineral oils and other oils such as glycerin and sorbitol. Particularly useful conditioning materials are cationic polymers. Conditioners of cationic polymer type can be chosen from those comprising units of at least one amine group chosen from primary, secondary, tertiary and quaternary amine groups that may either form part of the main polymer chain, or be borne by a side substituent that is directly attached to the main polymer chain, described hereinafter.

Suitable silicones include, but are not limited to: polyalkylsiloxane oils, linear polydimethylsiloxane oils containing trimethylsilyl or hydroxydimethylsiloxane endgroups, polymethylphenylsiloxane, polydimethylphenylsiloxane or polydimethyldiphenylsiloxane oils, silicone resins, organofunctional siloxanes having in their general structure one or a number of organofunctional group(s), the same or different, attached directly to the siloxane chain and mixtures thereof. Said organofunctional group(s) may be selected from: polyethyleneoxy and/or polypropyleneoxy groups, (per)fluorinated groups, thiol groups, substituted or unsubstituted amino groups, carboxylate groups, hydroxylated groups, alkoxylated groups, quaternium ammonium groups, amphoteric and betaine groups. The silicone can either be used as a neat fluid or in the form of a pre-formed emulsion.

Suitable silicones also include: silicones containing groups that may be ionized into cationic groups, for example aminosilicones containing at least 10 repeating siloxane $(Si(CH_3)_2-O)$ units within the polymer chain, with either terminal, graft, or a mixture of terminal and graft aminofunctional groups. Example functional groups are not limited to aminoethylaminopropyl, aminoethylaminoisobutly, aminopropyl. In the case of graft polymers, the terminal siloxane units can be $(CH_3)_3Si-O$, $R_{12}(CH_3)_2Si-O$, where $R_{12}$ can be either OH or $OR_{13}$, where $R_{13}$ is a C1-C8 alkyl group, or a mixture of both terminal groups. These silicones are also available as preformed emulsions.

Commercially available aminosilicones include those sold as DC-2-8566, DC 7224, DC-2-8220 by Dow Corning; SF1708, SM2125 by GE Silicones; Wacker Belsil ADM 653/ADM 1100/ADM 1600/ADM 652/ADM 6057E/ADM 8020 by Wacker Silicones; DC929, DC939, DC949 by Dow Corning; SM2059 by GE Silicones.

Suitable aminosilicones may also contain additional functional groups, particularly additional functional groups including polyoxyalkylene, the reaction product of amines and carbinols, and alky chains. Commercially available materials are known as methoxy PEG/PPG-7/3 Aminopropyl Dimethicone (e.g. Abil Soft AF100, by Degussa), or as Bis(C13-15 Alkoxy)PG Amodimethicone (e.g. DC 8500, by Dow Corning).

Suitable cationic polymers include, but are not limited to: polymers comprising units of at least one amine group chosen from primary, secondary, tertiary and quaternary amine groups that may either form part of the main polymer chain or be borne by a side substituent that is directly attached to the main polymer chain. Such cationic polymers generally have a number average molecular mass ranging from about 500 to about $5 \times 10^6$, alternatively from about 1000 to about $3 \times 10^6$. Preferably the cationic polymers are selected from polymers of the polyamine, polyamino amide and polyquaternary ammonium type.

Suitable polymers of the polyamine, polyamino amide and polyquaternary ammonium type include, but are not limited to:

1) Homopolymers and copolymers derived from acrylic or methacrylic esters or amides. Copolymers of these polymers may also comprise at least one unit derived from comonomers which may be chosen from the family of acrylamides, methacrylamides, diacetone acylamides, acrylamides and methacrylicamides substituted on the nitrogen with at least one group chosen from lower (C1-C4) alkyls, acrylic and methacrylic acids and esters thereof, vinylactams such as vinlypyrrolidone and vinylcaprolactam, and vinyl esters. Suitable examples include copolymers of acrylamide and of methacryloyloxyethyltrimethylammonium methosulfate, including polymers known as Polyquaternium-5 (e.g. commercially available under the trade name Reten 210/220/230/240/1104/1105/1006 by Hercules; Merquat 5/5 SF by Nalco); copolymers of vinylpyrrolidone and dimethylaminopropyl methacrylamide, including polymers known as Polyquaternium-28 (e.g. Gafquat HS-100 by ISP); coplolymers of vinyl pyrrolidone and dialkyaminoalkyl acrylates or methactylates, including polymers known as Polquaternium-11 (see Gafquat 440/734/755/755N by ISP; Luviquat PQ 11 PM by BASF; Polyquat-11 SL by Sino Lion); copolymers vinylpyrrolidone, dimethylaminopropyl methacrylamide and methacryloylaminopropyl lauryldimonium chloride, including polymers known as polyquaternium-55 (e.g. Styleze W-20 by ISP); copolymers of acrylic acid, acrylamide and methacrylamidopropyltrimonium chloride, including polymers known as Polyquatemium-53 (e.g. Merquat 2003 by Nalco); copolymers of dimethyaminopropylacrylate (DMAPA), acrylic acid and acrylonitrogens and diethyl sulphate, including polymers known as Polyquaternium-31 (e.g. Hypan QT100 by Lipo); copolymers of acrylamide, acrylamidopropyltrimonium chloride, 2-amidopropylacrylamide sulfonate, and dimethyaminopropylacrylate (DMAPA), including polymers known as polyquaternium-43 (e.g. Bozequat 4000 by Clairant); copolymers of acrylic acid, methylacrylate and methacrylamidopropyltrimonium chloride, including polymers known as Polyquaternium-47 (e.g. Merquat 2001/2001N by Nalco); copolymers of methacryloyl ethyl betaine, 2-hydroxyethyl methacrylate and methacryloyl ethyl trimethyl ammonium chloride, including polymers known as Polyquaternium-48 (e.g. Plascize L-450 by Goo Chemical); copolymers of acrylic acid diallyl dimethyl ammonium chloride and acrylamide, including polymers known as polyquaternium-39 (e.g. Merquat 3330/3331 by Nalco). Further suitable examples include copolymers of methacrylamide methacrylamido-propyltrimonium and methacryloylethyltrimethyl ammonium chloride and their derivatives, either homo or copolymerised with other monomers, including polymers known as Polyquaternium-8, Polyquatemium-9, Polyquaternium-12, Polyquaternium-13 Polyquaternium-14, Polyquaternium-15 (e.g. Rohagit KF 720 F by Rohm), Polyquaternium-30 (e.g. Mexomere PX by Chimex), Polyquaternium-33, Polyquatemium-35, Polyquaternium-36 (e.g. Plex 3074 L by Rhon), Polyquaternium 45 (e.g. Plex 3073L by Rohn), Polyquaternium 49 (e.g. Plascize L-440 by Goo Chemicals), Polyquaternium 50 (e.g. Plascize L-441 by Goo Chemicals), Polyquatemium-52.

2) Cationic polysaccharides, such as cationic celluloses and cationic galactomannan gums. Among the cationic polysaccharides that may be mentioned, for example, are cellulose ether derivatives comprising quaternary ammonium groups and cationic cellulose copolymers or cellulose derivatives grafted with a water-soluble quaternary ammonium monomer and cationic galactomannan gums. Suitable examples include copolymers of hydroxyethylcelluloses and diallyldimethyl ammonium chlorides, including polymers known as Polyquaternium-4 (e.g. Celquat L 200 and Celquat H 100 by National Starch); copolymers of hydroxyethylcelluloses and a trimethyl ammonium substituted epoxide, including polymers known as Polyquaternium-10 (e.g. AEC Polyquaternium-10 by A&E Connock; Catinal C-100/HC-35/HC-100/HC-200/LC-100/LC-200 by Toho; Celquat SC-240C/SC-230M by National Starch. Dekaquat 400/3000 by Dekker; Leogard GP by Akzo Nobel; RITA Polyquat 400/3000 by RITA; UCARE Polymer JR-125/JR-400/JR-30M/LK/LR 400/LR 30M by Amerchol); copolymers of hydroxyethylcelluloses and lauryl dimethyl ammonium substituted epoxides, including polymers known as Polyquaternium-24 (e.g. Quatrisoft polymer LM-200 by Amerchol); derivatives of hydroxypropyl guar, including polymers as guar hydroxypropyltrimonium chloride (e.g. Catinal CG-100, Catinal CG-200 by Toho; Cosmedia Guar C-261N, Cosmedia Guar C-261N, Cosmedia Guar C-261N by Cognis; DiaGum P 5070 by Freedom Chemical Diamalt; N-Hance Cationic Guar by Hercules/Aqualon; Hi-Care 1000, Jaguar C-17, Jaguar C-2000, Jaguar C-13S, Jaguar C-14S, Jaguar Excel by Rhodia; Kiprogum CW, Kiprogum NGK by Nippon Starch); hydroxypropyl derivatives of guar hydroxypropyltrimonium chloride, including polymers known as hydroxypropyl guar hydroxypropyltrimonium chloride (e.g. Jaguar C-162 by Rhodia).

3) Polyamino amide derivatives resulting from the condensation of polyalkylene polyamines with polycarboxylic acids followed by alkylation with difunctional agents. Among the derivative, mention may be made for example to adipic acid/dimethylaminohydroxypropyl/diethylenetriamine.

4) Polymers obtained by reaction of a polyalkylene polyamine comprising two primary amines groups and at last one secondary amine group with a decarboxylic acid chosen from diglycolic acids and saturated aliphatic dicarboxylic acids comprising from 3 to 8 carbon atoms. Suitable examples include the polymer adipic acid/epxoypropyl/diethylenetriamine.

5) Cyclopolymers of dialkdiallylamine or of dialkyldiallyammonium, including: Dimethyldiallyammonium chloride polymers, including polymers known as Polyquaternium-6 (e.g. Merquat 100 by Nalco; Mirapol 100 by Rhodia; Rheocare CC6 by Cosmetic Rheologies; AEC polyquaternium-6 by A&E Connock; Agequat 400 by CPS; Conditioner P6 by 3V Inc.; Flocare C106 by SNF; Genamin PDAC by Clariant; Mackemium 006 by McIntyre); copolymers of acrylamides and dimethyldiallylammonium chlorides monomers, including polymers known as Polyquaternium-7 (e.g. AEC Polyquaternium-7 by A&E Connock; Agequat-5008/C-505 by CPS; Conditioner P7 by 3V Inc.; Flocare C 107 by SNF, Mackernium 007/007S by McIntyre; ME Polymer 09W by Toho; Merquat 550/2200/S by Nalco; Mirapol 550 by Rhodia; Rheocare CC7/CCP7 by Cosmetic Rheologies; Salcare HSP-7/SC10/Super 7 by Ciba); copolymers of dimethyldiallylammoniumchlorides and acrylic acids, including polymers known as polyquaternary-22 (e.g. Merquat 280/Merquat 295 by Nalco).

6) Quaternary diammonium polymers comprising repeat units corresponding to [—N+(R1)(R2)-A1-N+(R3)(R4)-B1-][2X–], in which R1, R2, R3 and R4, which may be identical or different, are chosen from aliphatic, alicyclic and arylaliphatic radicals comprising from 1 to 20 carbon atoms and from lower hydroxyalkylaliphatic radicals, or R1, R2, R3 and R4, together or separately, constitute, with the nitrogen atoms to which they are attached, heterocycles optionally comprising a second heteroatom other then nitrogen, or R1, R2, R3 and R4, are chosen from liner or branched C1-C6 alkyl radicals substituted with at least one group chosen from nitrile, ester, acyl and amide groups and groups of —CO—O—R5-D and —CO—NH—R5-D wherein R5 is chosen from alkylene groups and D is chosen from quaternary ammonium groups. A1 and B1, which may be identical or different, are chosen from linear and branched, saturated or unsaturated polymethylene groups comprising 2 to 20 carbon atoms. The polymethylene groups may comprise, linked to or intercalated in the main ring, at least one entity chosen from aromatic rings, oxygen and sulphur atoms and sulphoxide, sulphone, disulphide, amino, alkylamino, hydroxyl, quaternary, ammonium, ureido, amide and ester groups, and X– is an anion derived from inorganic and organic acids. D is chosen from a glycol residue, a bis-secondary diamine residue, a bis-primary diamine residue or a ureylene group. Suitable examples include polymers known as Hexadimethrine chloride, where R1, R2, R3 and R4 are each methyl radicals, A1 is (CH2)3 and B1 is (CH2)6 and X=Cl; as polyquaternium-34 where R1 and R2 are ethyl radicals and R3 and R4 are methyl radicals and A1 is (CH2)3 and B1 is (CH2)3 and X=Br (e.g. Mexomere PAX by Chimax).

7) Polyquaternary ammonium polymers comprising repeating units of formula [—N+(R6)(R7)-(CH2)r-NH—CO—(CH2)q-(CO)t-NH—(CH2)s-N+(R8)(R9)-A-][2X−], in which R6, R7, R8 and R9 which may be identical or different, are chosen from a hydrogen atom and a methyl, ethyl, propyl, hydroxyethyl, hydroxypropyl, and —CH2CH2(OCH2CH2)pOH radicals, wherein p is equal to 0 or an integer ranging from 1 to 6, wherein R6, R7, R8 and R9 do not all simultaneously represent a hydrogen atom. R and s which may be identical or different are each an integer ranging from 1 to 6, q is equal to 0 or an integer ranging from 1 to 34 and X− is anion such as a halide. T is an integer chosen to be equal to 0 or 1. A is chosen from divalent radicals such as —CH2-CH2-O—CH2-CH2-. Suitable examples include: polymers known as polyquaternium-2, where r=s=3, q=0,t=0, R6, R7, R8 and R9 are methyl groups, and A is —CH2-CH2-O—CH2-CH2 (e.g. Ethpol PQ-2 from Ethox; Mirapol A-15 by Rhodia); as polyquaternium-17 where r=s=3, q=4, t=1 R6, R7, R8 and R9 are methyl groups, and A is —CH2-CH2-O—CH2-CH2; as Polyquaternium 18, where r=s=3, q=7, t=1 R6, R7, R8 and R9 are methyl groups, and A is —CH2-CH2-O—CH2-CH2; as the block copolymer formed by the reaction of Polyquaternium-2 with Polyquaternium-17, which are known as Polyquaternium 27 (e.g. Mirapol 175 by Rhodia).

8) Copolymers of vinylpyrrolidones and of vinylimidazoles and optionally vinylcaprolactums, including polymers known as Polyquaternary-16 formed from methylvinylimidazolium chlorides and vinylpyrrolidones (e.g. Luviquat FC370//FC550/FC905/HM-552 by BASF); copolymers of vinylcaprolactams and vinylpyrrolidones with methylvinylimidazolium methosulfates, including polymers known as Polyquaternium-46 (e.g. Luviquat Hold by BASF); copolymers of vinylpyrrolidones and quaternized imidazolines, including polymers known as polyquaternary 44 (e.g. Luviquat Care by BASF).

9) Polyamines such as Polyquart H sold by Cognis under the reference name polyethylene glycol (15) tallow polyamine.

10) Cross linked methacryloyloxy(C1-C4)alkyltri(C1-C4)alkylammonium salt polymers such as the polymers obtained by homopolymerisation of dimethylaminoethyl methacrylates quaternized with methyl chloride, or by copolymerisation of acrylamides with dimethylaminoethyl methacrylates quaternized with methyl chloride, the homo or copolymerisation being followed by crosslinking with a compound comprising olefinic unsaturation, such as methylenebisacrylamides, including polymers known as Polyquaternium-37 (e.g. Synthalen C N/CR/CU sold by 3V sigma; or as a dispersion in another media such as Salcare SC95/SC96 by Ciba; Rheocare CTH(E) by Cosmetic Rheologies) and polymers known as Polyquaternium-32 (e.g. sold as a dispersion in mineral oil such as Salcare SC92 by Ciba).

11) Further examples of cationic polymers include polymers known as Polyquaternium 51 (e.g. Lipidure-PMB by NOF), as Polyquaternium 54 (e.g. Qualty-Hy by Mitsui), as Polyquatemium 56 (e.g. Hairrol UC-4 by Sanyo chemicals), as Polyquaternium 87 (e.g. Luviquat sensation by BASF).

12) Silicone polymers comprising cationic groups and/or groups which may be ionised into cationic groups. Suitable examples include cationic silicones of the general formula (R10-N+(CH3)2)-R11-(Si(CH3)2-O)x-R11-(N+(CH3)2)-R10), where R10 is an alkyl derived from coconut oil, and R11 is (CH2CHOCH2O(CH2)3 and x is a number between 20 and 2000, including polymers known as Quaternium 80 (e.g. Abil Quat 3272/3474 sold by Goldschmidt); silicones containing groups which may be ionised into cationic groups, for example aminosilicones containing at least 10 repeating siloxane—(Si(CH3)2-O) units within the polymer chain, with either terminal, graft or a mixture of terminal and graft aminofunctional groups. Example functional groups are not limited to aminoethylaminopropyl, aminoethylaminoisobutly, aminopropyl. In the case of graft polymers, the terminal siloxane units can either be (CH3)3 Si—O or R12(CH3)2Si—O, where R12 can be either OH or OR13, where R13 is a C1-C8 alky group, or a mixture of both functional terminal groups. These silicones are also available as preformed emulsions. Polymer with terminal siloxane units of (CH3)3Si—O examples includes polymers known as trimethylsilylamodimethicone (e.g. DC-2-8566, DC 7224, DC-2-8220 by Dow Corning; SF1708, SM 2125 GE Silicones; Wacker Belsil ADM 653 by Wacker silicones). Further examples include polymers with terminal siloxane units of (R12O)(CH3)2Si—O where R12 can be either OH or OR13, where R13 is a C1-C8 alky group, or a mixture of both functional terminal groups, known as amodimethicone (e.g. Wacker Belsil ADM 1100/ADM 1600/ADM 652/ADM 6057E/ADM 8020 by Wacker Silicones; DC929, DC939, DC949 by Dow Corning; SM2059 by GE silicones). Silicones containing groups which may be ionised into cationic groups—for example silicones containing at least 10 repeating siloxane—(Si(CH3)2-O) units within the polymer chain, with either terminal, graft or a mixture of terminal and graft aminofunctional groups, together with additional functional groups. Additional functional groups can include polyoxyalkylene, the reaction product of amines and carbinols, alky chains. For example products known as methoxy PEG/PPG-7/3 Aminopropyl Dimethicone (e.g. Abil Soft AF100 by Degussa). For example products known as Bis (C13-15 Alkoxy) PG Amodimethicone (e.g. DC 8500 by Dow Corning).

In a preferred embodiment, the cationic polymer is selected from the group consisting of polyquaternium 37, polyquaternium 7, polyquaternium 22, polyquaternium 87, and mixtures thereof; particularly from the group consisting of polyquaternium 37, polyquaternium 22, and mixtures thereof.

Surfactants

The composition according to the present invention may further comprise a surfactant. Suitable surfactants generally have a lipophilic chain length of from about 8 to about 30 carbon atoms and can be selected from anionic surfactants, nonionic surfactants, amphoteric surfactants, cationic surfactants, and mixtures thereof.

Typically, the composition may comprise a total amount of surfactants ranging from about 1% to about 60%, alternatively from about 2% to about 30%, alternatively from about 8% to about 25%, alternatively from about 10% to about 20%, by weight of the total composition. The compositions may comprise a mixture of an anionic surfactant and an amphoteric surfactant with one or more nonionic surfactants. The composition may comprise a total amount of anionic surfactant ranging from about 0.1% to about 20%, alternatively from about 0.1% to about 15%, alternatively from about 5% to about 15%, by weight of the total composition; and a total amount of amphoteric and/or nonionic components, which may range independently from each other from about 0.1% to about 15%, alternatively from about 0.5% to about 10%, alternatively from about 1% to about 8%, by weight of the total composition.

Suitable anionic surfactants include, but are not limited to: salts (such as alkaline salts, for example, sodium salts, ammonium salts, amine salts, amino alcohol salts and magnesium salts) of the following compounds: alkyl sulphates, alkyl ether sulphates, alkylamido ether sulphates, alkylarylpolyether sulphates, monoglyceride sulphates; alkyl sulphonates, alkyl phosphates, alkylamide sulphonates, alkylaryl sulphonates, a-olefin sulphonates, paraffin sulphonates; alkyl sulphosuccinates, alkyl ether sulphosuccinates, alkylamide sulphosuccinates; alkyl sulphosuccinamates; alkyl sulphoacetates; alkyl ether phosphates; acyl sarcosinates; acyl isethionates; N-acyltaurates; and mixtures thereof. The alkyl or acyl radical of all of these various compounds, for example, comprises from 8 to 24 carbon atoms, and the aryl radical, for example, is chosen from phenyl and benzyl groups. Among the anionic surfactants, which can also be used, mention may also be made of fatty acid salts such as the salts of oleic, ricinoleic, palmitic and stearic acids, coconut oil acid or hydrogenated coconut oil acid; acyl lactylates in which the acyl radical comprises from 8 to 20 carbon atoms. Weakly anionic surfactants can also be used, such as alkyl-D-galactosiduronic acids and their salts, as well as polyoxyalkylenated (C6-C24) alkyl ether carboxylic acids, polyoxyalkylenated (C6-C24) alkylaryl ether carboxylic acids, polyoxyalkylenated (C6-C24) alkylamido ether carboxylic acids and their salts, for example, those comprising from 2 to 50 ethylene oxide groups, and mixtures thereof. Anionic derivatives of polysaccharides, for example carboxyalkyl ether of alkyl polyglucosides, can be also used. Nonionic surfactants are compounds that are well known (see, for example, in this respect "Handbook of Surfactants" by M. R. Porter, published by Blackie & Son (Glasgow and London), 1991, pp. 116-178).

Suitable non-ionic surfactants include, but are not limited to: polyethoxylated, polypropoxylated and polyglycerolated fatty acids, alkyl phenols, α-diols and alcohols comprising a fatty chain comprising, for example, from 8 to 18 carbon atoms, it being possible for the number of ethylene oxide or propylene oxide groups to range, for example, from 2 to 200 and for the number of glycerol groups to range, for example, from 2 to 30. Mention may also be made of copolymers of ethylene oxide and of propylene oxide, condensates of ethylene oxide and of propylene oxide with fatty alcohols; polyethoxylated fatty amides preferably having from 2 to 30 mol of ethylene oxide and their momoethanolamine and diethanolamine derivatives, polyglycerolated fatty amides, for example, comprising on average from 1 to 5, and such as from 1.5 to 4, glycerol groups; polyethoxylated fatty amines such as those containing from 2 to 30 mol of ethylene oxide; oxyethylenated fatty acid esters of sorbitan having from 2 to 30 mol of ethylene oxide; fatty acid esters of sucrose, fatty acid esters of polyethylene glycol, alkylpolyglycosides, N-alkylglucamine derivatives, amine oxides such as ($C_{10}$-$C_{14}$)alkylamine oxides or N-acylaminopropylmorpholine oxides.

Suitable amphoteric surfactants include, but are not limited to: aliphatic secondary and tertiary amine derivatives in which the aliphatic radical is chosen from linear and branched chains comprising from 8 to 22 carbon atoms and comprising at least one water-soluble anionic group (for example carboxylate, sulphonate, sulphate, phosphate or phosphonate); mention may also be made of ($C_5$-$C_{20}$)alkylbetaines, sulphobetaines, ($C_5$-$C_{20}$)alkylamido($C_1$-$C_6$)alkylbetaines or ($C_5$-$C_{20}$)alkylamido($C_1$-$C_6$)alkylsulphobetaines. Among the amine derivatives, mention may be made of the products sold as Miranol, as described, for example, in U.S. Pat. Nos. 2,528,378 and 2,781,354 and having the structures of: $R_2$—CONHCH$_2$CH$_2$—N$^+$($R_3$)($R_4$)(CH$_2$COO$^-$), (VI) in which: $R_2$ is chosen from alkyl radicals derived from an acid $R_2$—COOH present in hydrolysed coconut oil, and heptyl, nonyl and undecyl radicals, $R_3$ is a 1-hydroxyethyl group and $R_4$ is a carboxymethyl group; and of $R_5$—CONHCH$_2$CH$_2$—N(B)(C) (VII) wherein B represents —CH$_2$CH$_2$OX', C represents —(CH$_2$)$_z$—Y', with z=1 or 2, X' is chosen from the —CH$_2$CH$_2$—COOH group and a hydrogen atom, Y' is chosen from —COOH and —CH$_2$—CHOH—SO$_3$H radicals, $R_5$ is chosen from alkyl radicals of an acid $R_5$—COOH present in coconut oil or in hydrolysed linseed oil, alkyl radicals, such as $C_7$, $C_9$, $C_{11}$ and $C_{13}$ alkyl radicals, a $C_{17}$ alkyl radical and its iso form, and unsaturated $C_{17}$ radical. These compounds are classified in the CTFA dictionary, 5$^{th}$ edition, 1993, under the names disodium cocoamphodiacetate, disodium lauroamphodiacetate, disodium caprylamphodiacetate, disodium caprylamphodiacetate, disodium cocoamphodipropionate, disodium lauroamphodipropionate, disodium caprylamphodipropionate, disodium caprylamphodipropionate, lauroamphodipropionic acid, and cocoamphodipropionic acid. Salts of diethyl aminopropyl cocoaspartamid can be also used.

Suitable cationic surfactants include, but are not limited to, the quaternary ammonium salts A) to D) as defined hereinafter:

A) Quaternary ammonium salts of general formula (VIII) below:

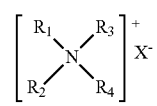

(VIII)

wherein X$^-$ is an anion chosen from halides (chloride, bromide and iodide), ($C_2$-$C_6$)alkyl sulphates, such as methyl sulphate, phosphates, alkyl and alkylaryl sulphonates, and anions derived from organic acids, such as acetate and lactate, and wherein $R_1$ to $R_4$ are as below in i) or ii).

i) Radicals $R_1$ to $R_3$, which may be identical or different, are chosen from linear and branched aliphatic radicals comprising from 1 to 4 carbon atoms, and aromatic radicals such as aryl and alkylaryl. The aliphatic radicals may comprise at least one hetero atom such as oxygen, nitrogen, sulphur and halogens. The aliphatic radicals may be chosen from: alkyl, alkoxy and alkylamide radicals. $R_4$ is chosen from linear and branched alkyl radicals comprising from 16 to 30 carbon atoms. A suitable cationic surfactant is, for example, a behenyltrimethylammonium salt (for example chloride).

ii) Radicals $R_1$ and $R_2$, which may be identical or different, are chosen from linear and branched aliphatic radicals comprising from 1 to 4 carbon atoms, and aromatic radicals such as aryl and alkylaryl. The aliphatic radicals may comprise at least one hetero atom such as oxygen, nitrogen, sulphur and halogens. The aliphatic radicals may be chosen from alkyl, alkoxy, alkylamide and hydroxyalkyl radicals comprising from about 1 to 4 carbon atoms. Radicals $R_3$ and $R_4$, which may be identical or different, are chosen from linear and branched alkyl radicals comprising from 12 to 30 carbon atoms, the said alkyl radicals comprise at least one function chosen from ester and amide functions. $R_3$ and $R_4$ may be chosen from ($C_{12}$-$C_{22}$)alkylamido($C_2$-$C_6$)alkyl and ($C_{12}$-$C_{22}$) alkylacetate radicals. A suitable cationic surfactant is, for example, a dicetyldimethyl ammonium salt (for example chloride);

B) Quaternary ammonium salts of imidazolinium of formula (IX) below:

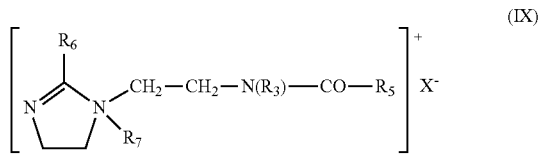

in which $R_5$ is chosen from alkenyl and alkyl radicals comprising from 8 to 30 carbon atoms, for example fatty acid derivatives of tallow, $R_6$ is chosen from a hydrogen atom, $C_1$-$C_4$ alkyl radicals and alkenyl and alkyl radicals comprising from 8 to 30 carbon atoms, $R_7$ is chosen from $C_1$-$C_4$ alkyl radicals, $R_5$ is chosen from a hydrogen atom and $C_1$-$C_4$ alkyl radicals, and $X^-$ is an anion chosen from halides, phosphates, acetates, lactates, alkyl sulphates, alkyl sulphonates and alkylaryl sulphonates. In one embodiment, $R_5$ and $R_6$ are, for example, a mixture of radicals chosen from alkenyl and alkyl radicals comprising from 12 to 21 carbon atoms, such as fatty acid derivatives of tallow, $R_7$ is methyl and $R_8$ is hydrogen. Such a product is, for example, Quaternium-27 (CTFA 1997) or Quaternium-83 (CTFA 1997), commercially available as "Rewoquat®" W75/W90/W75PG/W75HPG by Witco.

C) Diquaternary ammonium salts of formula (X):

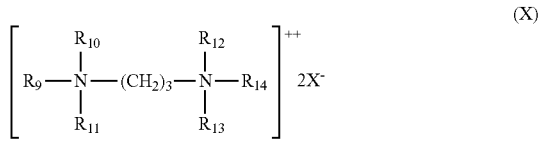

in which $R_9$ is chosen from aliphatic radicals comprising from about 16 to 30 carbon atoms, $R_{10}$, $R_{11}$, $R_{12}$, $R_{13}$ and $R_{14}$, which may be identical or different, are chosen from hydrogen and alkyl radicals comprising from 1 to 4 carbon atoms, and $X^-$ is an anion chosen from halides, acetates, phosphates, nitrates and methyl sulphates. Such diquaternary ammonium salts, for example, include propanetallowdiammonium dichloride.

D) Quaternary ammonium salts comprising at least one ester function, of formula (XI) below:

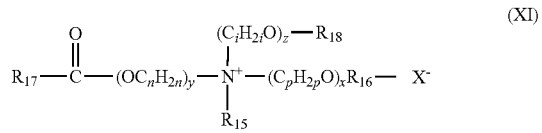

in which: R15 is chosen from C1-C6 alkyl radicals and C1-C6 hydroxyalkyl and dihydroxyalkyl radicals; R16 is chosen from: a radical R19C(O)-, linear and branched, saturated and unsaturated C1-C22 hydrocarbon-based radicals R20, and a hydrogen atom, R18 is chosen from: a radical R21C(O)-, linear and branched, saturated and unsaturated C1-C6 hydrocarbon-based radicals R22, and a hydrogen atom, R17, R19 and R21, which may be identical or different, are chosen from linear and branched, saturated and unsaturated C7-C21 hydrocarbon-based radicals; n, p and r, which may be identical or different, are chosen from integers ranging from 2 to 6; y is chosen from integers ranging from 1 to 10; x and z, which may be identical or different, are chosen from integers ranging from 0 to 10; X– is an anion chosen from simple and complex, organic and inorganic anions; with the proviso that the sum x+y+z is from 1 to 15, that when x is 0, then R16 is R20 and that when z is 0, then R18 is R22. In one embodiment, the ammonium salts of formula (XI) can be used, in which: R15 is chosen from methyl and ethyl radicals, x and y are equal to 1; z is equal to 0 or 1, n, p and r are equal to 2; R16 is chosen from: a radical R19C(O)—, methyl, ethyl and C14-C22 hydrocarbon-based radicals, and a hydrogen atom; R17, R19 and R21, which may be identical or different, are chosen from linear and branched, saturated and unsaturated C7-C21, hydrocarbon-based radicals; R18 is chosen from: a radical R21C(O)— and a hydrogen atom. Such compounds are commercially available as Dehyquart by Cognis, Stepanquat by Stepan, Noxamium by Ceca, and Rewoquat WE 18 by Rewo-Witco.

Functional, Synthetic and Experimental Aspects 2.0 General Aspects of Color Shift of Azomethine Dyes The color of a dye can be modified by addition of electron-donating or -withdrawing groups at specific positions in either the donor or acceptor portions of a dye molecule [8]. For azomethine dyes, the orientation of the electron-donating and electron-withdrawing substituents relative to one another, their degree of withdrawal or donation, and the effect on the planarity of the conjugated system all are important factors in the color and intensity produced [4]. For example, the color of the azomethine dye formed from a m-phenylenediamine (MPD) or a m-aminophenol (MAP) and a PPD derivative shifts bathochromically as one of the PPD nitrogens is substituted and electron density is increased. Substitution of the aromatic rings of the primary intermediate also can shift the color relative to the parent compounds, but these substitutions also can affect the coupling kinetics dramatically [9]. A strong electron-withdrawing group like cyano or nitro in the primary intermediate can drastically reduce or prevent oxidation to the benzoquinonediiminium ion, but if oxidation does occur, they increase the rate of coupling. Strong electron donating groups can increase the oxidation rate, but significantly decrease the coupling rate. The reverse effect on coupling rates is seen when the coupler is modified. Therefore, a balance is always sought.

2.1 Synthetic Approach

There is a challenge including a third electron-donating group in the acceptor portion of the azomethine when that group is an amine or hydroxyl group. Assembly of an azomethine via $S_NAr$ reactions or oxidative coupling in such a situation challenges both an expedient oxidation rate and an expedient coupling rate. Groups such as phthalimide or oxazolidinone to mask amino groups may lessen the challenge.

The m-aminophenol substituted with an electron-donating group such as the 2-hydroxyethylamino group can be prepared to investigate these challenges. The 2-hydroxyethylamino group is well-known in oxidation dye chemistry, it is generally easy to introduce, the final dyes generally are not prone to side reactions such as hydrolysis, and it aids in solubility.

There are two main ways to prepare the azomethine dyes. The first approach is modeled after Corbett's work of aminoindamines [11] and the work of Bailey, et al. on PPD-resorcinol oligomerization [7]. By this approach, the desired azomethine dye is assembled via a series of $S_NAr$ reactions and reductions to form the penultimate diphenylamine, which is then oxidized to the desired compound. However, when the desired compound is a m-aminophenol derivative, $S_NAr$ substitution, particularly the second substitution, is predicted to be sluggish at best (Scheme 3, PPD is para phenylene diamine).

Scheme 3: Example preparation of azomethine (indoaniline) dye 11 containing an electron-donating aminoalkyl group in the donor portion of the molecule via multiple SnAr reactions.

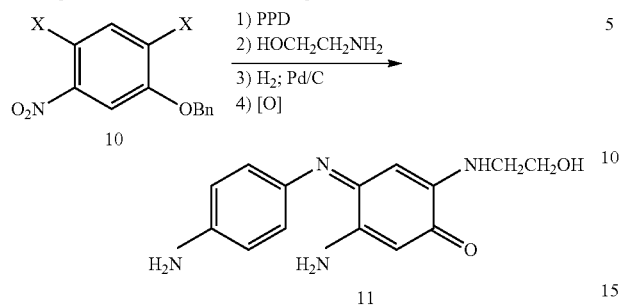

2.2 Synthetic Design of New Azomethines Via Oxidative Coupling

The second way is to oxidatively couple the precursor primary intermediate, PPD, and m-coupler 12, and then to do a series of purifications to obtain the desired compound as shown by Scheme 4.

Scheme 4: Depiction of oxidative coupling of PPD (1) and 5-amino-2-((2-hydroxyethyl)amino)phenol (12) to generate 5-amino-4-((4-aminophenyl)imino)-2-((2-hydroxyethyl)amino) cyclohexa-2,5-dien-1-one (11).

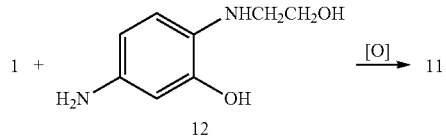

This approach also has several issues. Both 1 and 12 are readily oxidized and can act as primary intermediates, and in fact, 12 can form two oxidized species: a p-benzoquinonediimine and an o-benzoquinonemonoimine. This complication will lead to a very complex reaction mixture. The question is how to overcome this issue.

2.3 Synthetic Design of New Azomethines Via Oxidative Coupling of Couplers with Reduced Electron Density and Masked Functional Groups The oxazolidinone ring could serve as an appropriate masked 2-hydroxyethylamino group. The ring also may be stable under the normal oxidative hair dyeing conditions (pH 8.5-pH 11, $H_2O_2$).

An oxazolidinone attached to the aromatic ring will withdraw electrons, but it is unknown how it would affect the ability of a compound containing it to undergo oxidative coupling, and what the effect would be on the color of the azomethine dye formed. Investigation of the oxazolidinone derivative of m-aminophenol and its conversion to azomethine dyes would answer these questions. Scheme 5 provides the sequence for carrying out part of this investigation.

Scheme 5: Synthetic route for preparation of azomethine dyes based on p-phenylenediamine with an oxazolidinone or 2 hydroxyethylamino group on the acceptor portion of the dye.

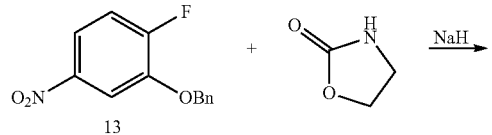

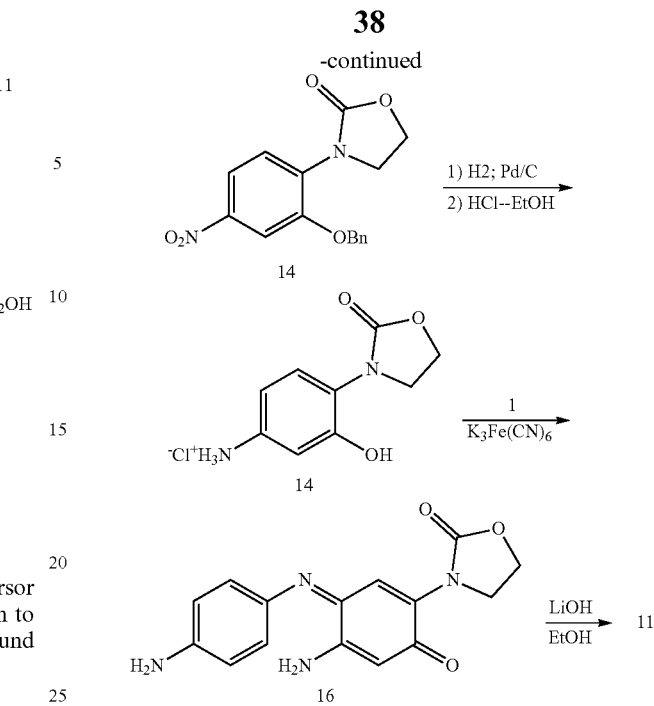

The oxazolidinone is introduced into 13 directly by substitution for the fluorine atom of 13, mediated by the non-nucleophilic base, NaH. Reaction in DMF was generally complete in 2 hours, and 14 was purified easily on a CombiFlash HPLC (hexanes-EtOAc linear gradient on silica). Reduction of the nitro group and hydrogenolysis of the benzyl ether were accomplished simultaneously in ethanol over Pd/C at 75 psig. Coupling can be mediated by bubbling air through an alkaline solution of 1 and 15 but the reaction is slow and by-products form. Potassium ferricyanide oxidation gave a cleaner product. Although 16 needed to be separated from the resultant ferrocyanide salt, this was easily accomplished by filtration through Celite followed by column chromatography. Stirring 16 with LiOH in ethanol at 20° C. gave 2-hydroxyethylamino derivative 11, and these new dyes (11 and 16) now could be compared to known PPD-based azomethine dyes.

Both the 2-hydroxyethylamino group and the oxazolidinone groups shifted the visible color significantly, and in opposite directions relative to the parent dye (PPD-MAP).

2.4 Expanding the Series of Electron-Donating and Electron-Withdrawing Auxochromes Phthalimide as a substituent was also investigated to determine its effect on color. It is electron-withdrawing and has the added advantage that it is also an easily removed amine protecting group. This means that data could be obtained for another azomethine dye with an electron-donating group in the acceptor portion. The phthalimide derivative (19, Scheme 6) was prepared by the same approach as was used for oxazolidinone compound 16.

Scheme 6: Synthetic route for preparation of azomethine dyes based on p-phenylenediamine with a phthalimide group in the acceptor portion of the dye.

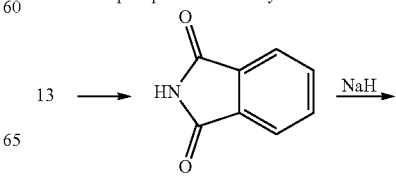

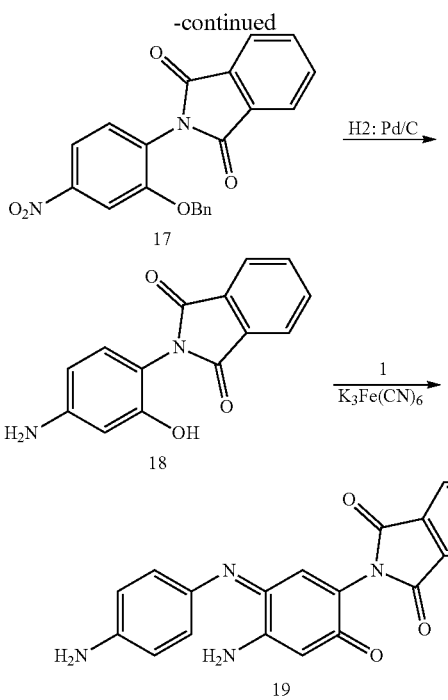

2.5 Effect of Electron-Donating and Electron-Withdrawing Auxochromes on Solution Color and Oxidatively Dyed Tress Color Table 1 compares the series of azomethine dyes that are substituted in the acceptor portion of the molecule with either electron-donating (-Me and —NHCH$_2$CH$_2$OH) or the electron-withdrawing (oxazolidinone or phthalimide) groups to the unsubstituted parent, PPD-MAP azomethine (20). It is clear from the table that as electron-donating groups are bonded to the ring of the acceptor portion, color can be shifted more toward orange (hypsochromically). Relative to the parent azomethine, the colors of the unprotected amine substituted derivatives were shifted at least 40 nm.

TABLE 1

Variation of $\lambda_{max}$ and ε as a function of substitution of azomethine with electron-donating or electron withdrawing groups in the acceptor portion of the dye. Absorbance spectra of the purified dye were acquired on a Waters Acuity ™ UPLC with a PDA eλ detector. For 4 and 16, absorbance spectra for determination of extinction coefficients were acquired on a Cary 100 UV/visible spectrophotometer.

| Dye | $\lambda_{max}$ (nm) | ε (M$^{-1}$ cm$^{-1}$) |
|---|---|---|
| 16 | 531 | 12,400 |
| 20 | 516 | |
| 19 | 504 | |
| 4 | 502 | 10,500 |
| 11 | 468 | |

2.6 Effect on Color of Orbital Overlap of Auxochrome with Chromophore

For compound 16, the color was shifted bathochromically by about 20 nm, making it more violet than the parent PPD-MAP. For phthalimide dye 19, although there are two electron-withdrawing carbonyl groups attached to the amine, the color was similar to the PPD-AHT analog, which has a weakly electron-donating methyl group.

Azomethine dye 16 was particularly interesting because unlike the ureido group, the oxazolidinone moiety did not appear to significantly decrease coupling rate, and unlike the phthalimide group, it was stable at pH 10 and also to the strongly nucleophilic peroxy anion (HOO$^-$).

2.7 Effect of Electron-Withdrawing Group on Competition Kinetics

Although 15 and 18 gave intense colors on hair when reacted with PPD, it was still important to determine whether the rate of coupling is competitive with the current couplers. 19 can be hydrolyzed in pH 10 buffer, and 16 is stable under those conditions, 15 can be used for the competition kinetics to make the interpretation more straightforward. PPD, 15, AHT, and K$_3$Fe(CN)$_6$ were combined in a ratio of 1:1:1:4, and the reaction was monitored by UPLC. It is known that electron-withdrawing groups in the coupler decrease the rate of color formation [9], and the rate of color formation from PPD and 15 was somewhat slower than for PPD and AHT. At the completion of the reaction, the product mixture was 40% of 16 and 60% of the PPD-AHT azomethine dye, showing that the rate of coupling is ca. 67% that of PPD and AHT, indicating that 15 can compete effectively with standard current couplers in hair-color shades.

2.8 Expanding to the 4,5-diaminopyrazoles

The investigation also determined whether 15 would couple with a 4,5-diaminopyrazole derivative to give a redder color than standard couplers give with them. $N^1$-Hexyl-4,5-diaminopyrazole (21) coupled with compound 15 (Scheme 7) in the presence of ferricyanide, as described previously for PPD. The reaction was complete quickly, and it seemed that these also could be useful azomethine dyes.

Scheme 7: Preparation of azomethine dye from $N^1$-hexyl-4,-5-diaminopyrazole (22) and oxazolidinone-containing m-aminophenol coupler 15. The azomethine dye was formed in aqueous ethanol (pH 10) by mixing 21,15, and $K_3Fe(CN)_6$ in a ration of 1:1:4.

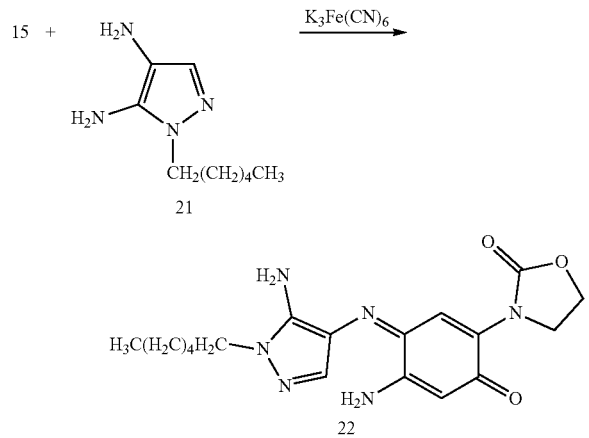

Compounds 25a-25d were prepared by the same procedure to give a complete series that included the parent compounds (25a and 25b), the azomethine dye with the electron-withdrawing oxazolidinone, and the electron-donating methyl groups (25c and 25d; Scheme 8).

Scheme 8: Preparation of azomethine dyes from based on 4,5-diaminopyrazole with substitution on the acceptor (coupler) portion of the dye. The azomethine dyes were formed in aqueous ethanol (pH 10) by mixing the 4,5-diaminopyrzole with coupler and $K_3Fe(CN)_6$ in a ratio of 1:1:4.

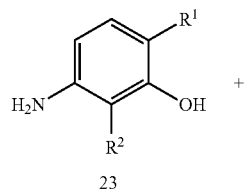

23

For 23
a: $R^1 = R_2 = $ ———H
b: $R^1 = R_2 = $ ———$CH_3$

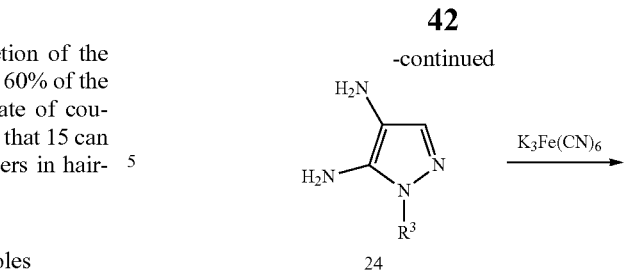

24

For 24
a: $R^3 = $ ———$CH_2(CH2)_4CH_3$
b: $R^3 = $ ———$CH_2CH_2OH$

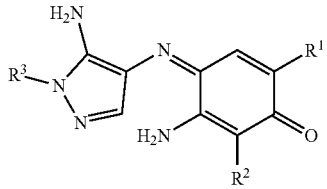

25

For 25
a: $R^1 = R_2 = $ ———H, $R_3 = $ ———$CH_2(CH2)_4CH_3$
b: $R^1 = R_2 = $ ———H, $R_3 = $ ———$CH_2CH_2OH$
c: $R^1 = R_2 = $ ———$CH_3$, $R^3 = $ ———$CH_2(CH2)_4CH_3$
d: $R^1 = R_2 = $ ———$CH_3$, $R^3 = $ ———$CH_2CH_2OH$

Relative to the azomethine formed with 2,6-dimethyl-3-aminophenol, which contained two weakly electron-donating substituents, the absorbance maximum for 22 was shifted bathochromically by ca. 20 nm for the azomethine dyes. Also interesting was the fact that there was no effect on color whether the pyrazole nitrogen was substituted with 2-hydroxyethyl or hexyl.

TABLE 2

Variation of $\lambda_{max}$ and ε as a function of substitution of acceptor portion of dyes formed from m-aminophenol derivatives and 4,5-diaminopyrazoles. Absorbance spectra of the purified dye were acquired on a Waters Acuity ™ UPLC with a PDA eλ detector. For 13 and 25c, absorbance spectra for determination of extinction coefficients were acquired on a Cary 100 UV/visible spectrophotometer.

| Dye | $\lambda_{max}$ (nm) | ε ($M^{-1}$ $cm^{-1}$) |
|---|---|---|
| 22 | 499.3 | 26,200 |
| 25a | 487.1 | |

TABLE 2-continued

Variation of $\lambda_{max}$ and ε as a function of substitution of acceptor portion of dyes formed from m-aminophenol derivatives and 4,5-diaminopyrazoles. Absorbance spectra of the purified dye were acquired on a Waters Acuity ™ UPLC with a PDA eλ detector. For 13 and 25c, absorbance spectra for determination of extinction coefficients were acquired on a Cary 100 UV/visible spectrophotometer.

| Dye | $\lambda_{max}$ (nm) | ε ($M^{-1}$ $cm^{-1}$) |
|---|---|---|
| 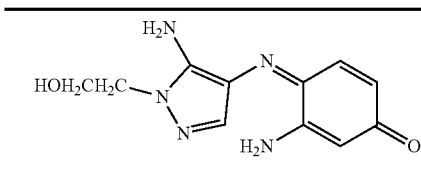 25b | 487.1 | |
| 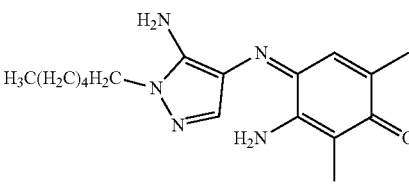 25c | 477.4 | 21,500 |
| 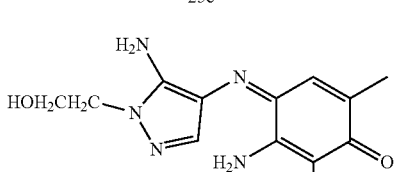 25d | 477.4 | |

2.9 Hair Dyeing Under Oxidative Conditions

Both PPD and the 4,5-diaminopyrazoles gave colors in solution with both the oxazolidinone- and phthalimide-modified MAPs that could be desirable colors. Virgin natural white tresses were dyed to determine whether, in fact, the subject dyes could be useful in oxidation dyeing products. Compound 11 was not compared to these materials using normal oxidative dyeing procedures. The couplers from which they would need to be formed also act as primary intermediates, just as the well-known o-aminophenols. The analysis was limited to the intermediates in this study that would act solely as couplers.

With PPD, the trend on hair was the same as in solution; the oxazolidinone-containing coupler (16) had the bluest color, i.e. the b*value was the lowest, and the hue angle (h) was shifted furthest toward the blue (Table 3). Because the interest is in the practical utility of such oxidation dye systems, the common coupler MAP was included, although it should be noted MAP is not a blocked coupler and can form trimeric materials [16,17], unlike the AHT, 15, and 19. Consequently, use of MAP does not yield only the color of the dimer as the other materials do. Absorbance spectra were measured using the purified PPD-MAP dimer as a standard for comparison.

TABLE 3

Color readings taken with a Konica Minolta CM-3700A spectrophotometer using a 1 cm aperture width for virgin natural white hair dyed with a combination of using PPD and either 15, MAP, AHT, or 19 in a 75:20:5 water-ethanol-ammonium hydroxide solution at pH 10 in an incubator (30° C.) for 30 minutes.

| Dye | L* | a* | b* | C | h |
|---|---|---|---|---|---|
| 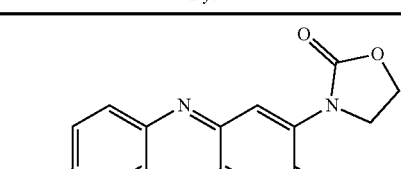 16 | 24.09 | 7.02 | −3.105 | 7.67 | 336.14 |
| 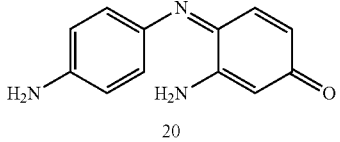 [SMILES: NC1=CC(=O)C=C/C1=N/c1ccc(N)cc1] 20 | 18.85 | 3.36 | 0.71 | 3.44 | 12 |
| 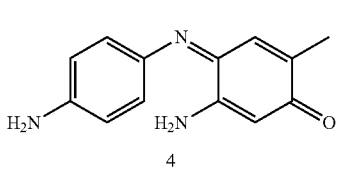 [SMILES: CC1=C/C(=N/c2ccc(N)cc2)C(N)=CC1=O] 4 | 17.9 | 8.56 | 0.06 | 8.56 | 359.74 |

TABLE 3-continued

Color readings taken with a Konica Minolta CM-3700A spectrophotometer using a 1 cm aperture width for virgin natural white hair dyed with a combination of using PPD and either 15, MAP, AHT, or 19 in a 75:20:5 water-ethanol-ammonium hydroxide solution at pH 10 in an incubator (30° C.) for 30 minutes.

| Dye | L* | a* | b* | C | h |
|---|---|---|---|---|---|
| 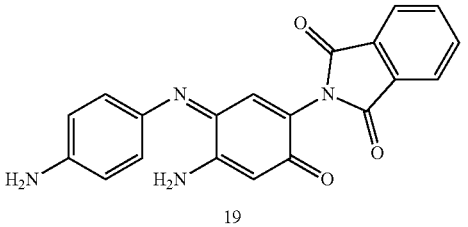 [SMILES: NC1=CC(=O)C(N2C(=O)c3ccccc3C2=O)=C/C1=N/c1ccc(N)cc1] 19 | 18.33 | 2.9 | 0.08 | 2.98 | 346.9 |

4,5-Diaminopyrazoles are used in oxidative dye products to give brilliant orange to reddish colors on hair. Solution studies showed that dimer 22 had the highest absorbance wavelength in the series, and should could give a purer red on hair, i.e. a higher a*value and a b*value closer to zero, also represented as a hue angle close to 0°. Again, the parent coupler of the series (MAP) can form a trimer, and it did give a reddish color on hair, although the a*value for 25a was significantly lower than for 22. This was offset by less of a yellow contribution (lower b*). It also should be noted that for these tresses dyed at equimolar concentrations, the tress for 25a was significantly more intense, so at equal intensity (to 22) the color may not have appeared as red. The difference in hue angle for tresses dyed with 22 and 25a were similar, with the tress dyed with 25a being only 0.70 more red. Consistent with the solution experiments, 25c was significantly less red that the others, due to the two electron-donating groups in the acceptor portion (Table 4).

TABLE 4

Color readings taken with a Konica Minolta CM-3700A spectrophotometer using a 1 cm aperture width for virgin natural white hair dyed with a combination of using 24a or 24b and either 15, MAP, or AHT in a 75:20:5 water-ethanol-ammonium hydroxide solution at pH 10 in an incubator (30° C.) for 30 minutes.

| Dye | L* | a* | b* | C | h |
|---|---|---|---|---|---|
| 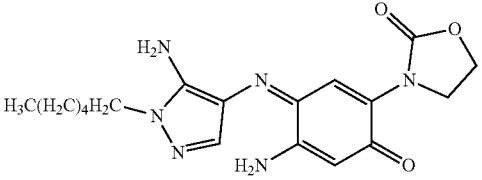 22 | 30.18 | 32.29 | 10.11 | 33.84 | 17.38 |
| 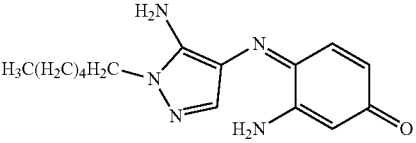 25a | 21.09 | 18.45 | 5.52 | 19.26 | 16.64 |
| 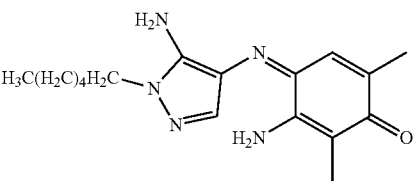 25c | 31.38 | 39.96 | 23.62 | 46.42 | 30.59 |

EXAMPLES 3.1 The following are non-limiting examples of compositions of the present invention. The examples are given solely for the purpose of illustration and are not to be construed as limitations of the present invention, as many variations thereof are possible without departing from the spirit and scope of the invention, which would be recognized by one of ordinary skill in the art. All concentrations are listed as weight percent, unless otherwise specified.

3.2 Instruments $^1$H NMR were recorded on a Varian Unity-Inova 300 MHz NMR spectrometer. Spectra were referenced internally to solvent residual peaks. MS was carried out on a Waters Micromass ZQ spectrometer and HRMS was done on a ThermoScientific Orbitrap Elite. Thin-layer chromatography (TLC) was performed using Analytech silica gel plates with fluorescent indicator. Flash chromatography was performed using a Teledyne Isco CombiFlash EZ Prep chromatography system equipped with a UV detector. UPLC was performed on a Waters Acuity™ system with a PDA e, Detector. Color readings were taken on a Konica Minolta CM-3700A spectrophotometer, using a 1 cm aperture width, with D65 illumination and characterized by the L* value. An L* of 100 is considered white and L* of 0 is considered black, therefore the higher the L* value the lower the color intensity. Absorbance spectra to calculate extinction coefficients were obtained on a Cary 100 UV/visible spectrophotometer.

3.3 Methods

3.3.1 Synthesis of 3-(2-(benzyloxy)-4-nitrophenyl)oxazolidin-2-one (14)

To a dry, 50 mL round bottom flask was added 2-(benzyloxy)-1-fluoro-4-nitrobenzene (2.65 g, 10.7 mmol) and DMF (15 mL). To another dry, 50 mL round bottom flask was added 2-oxazolidinone (1.00 g, 11.5 mmol) as a white solid and DMF (20 mL). To the solution was added 60% NaH in mineral oil (0.440 g, 11.0 mmol). The suspension was sonicated at room temperature for 10 min, then stirred magnetically for 40 min until the evolution of hydrogen ceased. The DMF solution of 1-fluoro-2,4-dinitrobenzene was then transferred to the flask containing 2-oxazolidinone sodium salt. After complete addition the reaction was allowed to stir at room temperature and monitored by UPLC. The color of the solution changed from pale yellow to near black. Once the reaction is complete, DMF was removed under vacuum and the reaction mixture was purified by flash chromatography (SiO$_2$, hexane/EtOAc gradient) to afford 3.13 g pale yellow crystalline solid (93% yield). $^1$H NMR (300 MHz, CDCl$_3$): δ 4.10 (dd, 2H, J$_1$=6.9 Hz, J$_2$=8.7 Hz), 4.48, (dd, 2H, J$_1$=6.9 Hz, J$_2$=8.7 Hz), 5.23 (s, 2H), 7.43~7.48 (m, 5H), 7.70 (d, 1H, J=9.3 Hz), 7.94~7.96 (m, 2H). HRMS Found: [M+H]+ 315.0975; molecular formula C$_{16}$H$_{14}$N$_2$O$_5$ requires [M+H]+ 315.0975.

3.3.2 Synthesis of 3-hydroxy-4-(2-oxooxazolidin-3-yl)benzenaminium chloride (15)

To a Fisher Porter tube was added 10 wt % Pd/C (100 mg) and 3-(2-(benzyloxy)-4-nitrophenyl)oxazolidin-2-one (1.0 g, 3.2 mmol) crystalline solid. EtOH (15 mL) and a stir bar were added to the Fisher Porter tube. To the suspension was added dry ice (0.5 g). The vessel was then coupled with the gauge while leaving the vent open until dry ice completely disappeared. The vessel was then charged with H$_2$ (75 psig) and vented to the air. The charge-vent cycle was repeated six times. The vessel was then charged with Hz (75 psig) and stirred magnetically at room temperature. After 24 h the stirring was stopped to allow the carbon to precipitate. The reduction was considered complete when the clear solution on top showed no hint of yellow. The remaining pressure was then released. Concentrated aqueous HCl (0.5 mL, 6.1 mmol) and water (10 mL) were then added to the suspension. The suspension was then filtered through a 0.4 µm syringe filter to afford a clear and colorless solution. The solution was concentrated by vacuo to afford a grayish solid in quantitative yield. $^1$H NMR (300 MHz, CDCl$_3$): δ 4.06 (t, 2H, J=8.0 Hz), 4.57, (t, 2H, J=8.0 Hz), 6.95 (dd, 1H, J$_1$=2.4 Hz, J$_2$=8.4 Hz), 7.06 (d, 1H, J=2.4 Hz), 7.47 (d, 1H, J=8.4 Hz). HRMS Found: [M+H]+ 195.0766; molecular formula C$_9$H$_{11}$ClN$_2$O$_3$ requires [M+H]+ 195.0764.

3.3.3 Synthesis of 3-(4-amino-3-((4-aminophenyl)imino)-6-oxocyclohexa-1,4-dien-1-yl)oxazolidin-2-one (16)

To a 250 mL Erlenmeyer flask was added K$_3$Fe(CN)$_6$ (12.18 g, 37.0 mmol) and water (120 mL). The flask was then capped and sonicated to quickly dissolve all salt to produce a homogeneous yellow solution. To a 500 mL Erlenmeyer flask was added 1,4-diaminobenzene (1.00 g, 9.25 mmol) and 3-(4-amino-2-hydroxyphenyl)oxazolidin-2-one hydrochloride (2.00 g, 8.67 mmol). To the mixture was then added water (100 mL), ethanol (20.0 mL) and 28% ammonium hydroxide aq. solution (10.0 mL) to completely dissolve the dye precursors. The tint solution turned light purple. The K$_3$Fe(CN)$_6$ solution was then transferred to the flask containing the dye precursors. The solution immediately turned purple black. The reaction mixture was then magnetically stirred for 30 min. After which solvents were removed by vacuo. The residual solid was dry loaded onto silica and purified with the CombiFlash automated flash chromatography system with CH$_2$Cl$_2$/MeOH as mobile phase. All purple fractions were collected, combined and purified again on the same system with a hexanes/EtOAc gradient as the mobile phase. 0.613 g of the final product was obtained as a purplish black tar-like solid (23.7% yield). $^1$H NMR (300 MHz, CD$_3$OD): δ 3.62 (t, 2H, J=8.4 Hz), 4.46 (t, 2H, J=8.4 Hz), 5.69 (s, 1H), 6.77 (d, 2H, J=8.7 Hz), 7.02 (d, 2H, J=8.7 Hz), 7.30 (s, 1H). HRMS Found: [M+H]+ 299.1139; molecular formula C$_{15}$H$_{14}$N$_4$O$_3$ requires [M+H]+ 299.1139.

3.3.4 Synthesis of 5-amino-4-((4-aminophenyl)imino)-2-((2-hydroxyethyl)amino)cyclohexa-2,5-dien-1-one (11)

To a scintillation vial was added the violet dye, 3-(4-amino-3-((4-aminophenyl)imino)-6-oxocyclohexa-1,4-dien-1-yl)oxazolidin-2-one (25.0 mg, 0.084 mmol). LiOH (20.0 mg, 0.84 mmol) and ethanol (6.0 mL) were then added to the vial. The scintillation vial was then capped and magnetically stirred at ambient temperature. The reaction was monitored by UPLC to make sure that all starting material was converted to product. After 2 hours, the crude reaction mixture was loaded directly on a 40 g CombiFlash silica gel column and flushed with a CH$_2$Cl$_2$/MeOH gradient on automated CombiFlash chromatography system. The colored fractions were collected, concentrated, and purified again by the same method to afford a brownish red dye (20.0 mg, 87.6% yield). $^1$H NMR (300 MHz, CD$_3$OD): δ 3.08 (t, 2H, J=5.6 Hz), 3.67 (t, 2H, J=5.6 Hz), 5.60 (s, 1H), 6.69 (d, 2H, J=8.4 Hz), 6.74 (s, 1H), 6.78 (d, 2H, J=8.4 Hz). HRMS Found: [M+H]+ 273.1347; molecular formula C$_{14}$H$_{16}$N$_4$O$_2$ requires [M+H]+ 273.134.

3.3.5 Synthesis of 2-(4-amino-2-hydroxyphenyl) isoindoline-1,3-dionehydrochloride salt (18)

To a Fisher Porter tube was added 10 wt % Pd/C (50 mg) and 2-(2-hydroxy-4-nitrophenyl)isoazomethineline-1,3-dione (0.60 g, 2.1 mmol) brown powder. EtOH (10 mL) and a stir bar were added to the Fisher Porter tube. To the suspension was added dry ice (0.5 g). The vessel was then coupled with the gauge while leaving the vent open until dry ice completely disappeared. The vessel was then charged with H$_2$ (75 psig) and vented to the air. The charge-vent cycle was repeated six times. The vessel was then charged with H$_2$ (75 psig) and stirred magnetically at room temperature. After 24 h the stirring was stopped to allow the carbon to precipitate. The reduction was considered complete when the clear solution on top showed no hint of yellow. The remaining pressure was then released. Concentrated aq. HCl (0.25 mL, 3.0 mmol) and water (10 mL) were then added to the suspension. The suspension was then filtered through a 0.4 µm syringe filter to afford a clear and colorless solution. The solution was concentrated by vacuo to afford a white powder in quantitative yield. $^1$H NMR (300 MHz, CD$_3$OD): δ 7.02 (dd, 1H, J$_1$=2.3 Hz, J$_2$=8.6 Hz), 7.10 (d, 1H, J=2.3 Hz), 7.43 (d, 1H, J=8.6 Hz), 7.90-8.0 (m, 4H). HRMS Found: [M+H]+ 255.0766; molecular formula C$_{14}$H$_{10}$N$_2$O$_3$ requires [M+H]+ 255.0764.

3.3.6 2-(4-amino-3-((4-aminophenyl)imino)-6-oxo-cyclohexa-1,4-dien-1-yl)isoindoline-1,3-dione (19)

To a scintillation vial was added K$_3$Fe(CN)$_6$ (0.378 g, 1.15 mmol) and water (12 mL). The vial was then capped and sonicated to quickly dissolve all salt to produce a homogeneous yellow solution. To a 100 mL pear shaped flask was added 1,4-diaminobenzene (31 mg, 0.29 mmol) and 2-(4-amino-2-hydroxyphenyl)isoindoline-1,3-dione hydrochloride (81 mg, 0.28 mmol). To the mixture was then added water (10 mL), ethanol (5.0 mL) and 28% ammonium hydroxide aq. solution (1.0 mL) to completely dissolve the dye precursors. The tint solution turned light purple. The K$_3$Fe(CN)$_6$ solution was then transferred to the flask containing the dye precursors. The solution immediately turned purple black. The reaction mixture was then magnetically stirred for 30 min. After which solvents were removed under vacuum. The residual solid was dry loaded onto silica and purified with the CombiFlash automated flash chromatography system with a CH$_2$Cl$_2$/MeOH gradient as mobile phase. All purple fractions were collected, combined and purified again on the same system with CH$_2$Cl$_2$/MeOH as mobile phase. Forty-seven mg of the final product was obtained as a purplish black tar-like solid (47% yield). $^1$H NMR (300 MHz, D$_3$OD): δ 5.71 (s, 1H), 6.81 (d, 2H, J=8.7 Hz), 6.93 (s, 1H), 7.01 (d, 2H, J=8.7 Hz), 7.51~7.61 (m, 4H). HRMS Found: [M+H]+ 359.1140; molecular formula C$_{20}$H$_{14}$N$_4$O$_3$ requires [M+H]+ 359.1139.

3.3.7 Synthesis of 3-(4-amino-3-((5-amino-1-hexyl-1H-pyrazol-4-yl)imino)-6-oxocyclohexa-1,4-dien-1-yl)oxazolidin-2-one (22)

To a 100 mL Erlenmeyer flask was added K$_3$Fe(CN)$_6$ (6.09 g, 18.5 mmol) and water (80 mL). The flask was then capped and sonicated to quickly dissolve all salt to produce a homogeneous yellow solution. To a 250 mL Erlenmeyer flask was added 4,5-diamino-1-hexyl-1H-pyrazole hemisulfate (1.04 g, 4.5 mmol) and 3-(4-amino-2-hydroxyphenyl) oxazolidin-2-one hydrochloride (1.00 g, 4.34 mmol). To the mixture was then added water (50 mL), ethanol (10.0 mL) and 28% ammonium hydroxide aq. solution (5.0 mL) to completely dissolve the dye precursors. The tint solution turned light red. The K$_3$Fe(CN)$_6$ solution was then transferred to the flask containing the dye precursors. The solution immediately turned dark red. The reaction mixture was then magnetically stirred for 30 min. After which solvents were removed by vacuo. The residual solid was dry loaded onto silica and purified with the CombiFlash automated flash chromatography system with CH$_2$Cl$_2$/MeOH as mobile phase. All red fractions were collected, combined and purified again on the same system with a hexanes/EtOAc gradient as mobile phase. 0.593 g of the final product was obtained as a dark red tar-like solid (36.7% yield). $^1$H NMR (300 MHz, CD$_3$OD): δ 0.89 (br., 3H), 1.31 (br., 6H), 1.73 (br., 2H), 3.86 (t, 2H, J=6.0 Hz), 4.20 (t, 2H, J=7.8 Hz), 4.44 (t, 2H, J=7.8 Hz), 5.54 (s, 1H), 7.48 (s, 1H), 7.57 (s, 1H). HRMS Found: [M+H]+ 373.1983; molecular formula C$_{18}$H$_{24}$N$_6$O$_3$ requires [M+H]+ 373.1983.

3.3.8 3-amino-1-(2-hydroxyethyl)-1H-pyrazol-4-yl) imino)-26-dimethylcyclohexa-2,5-dien-1-one (25d)

To a 100 mL Erlenmeyer flask was added K$_3$Fe(CN)$_6$ (6.09 g, 18.5 mmol) and water (50 mL). The flask was then capped and sonicated to quickly dissolve all salt to produce a homogeneous yellow solution. To a 250 mL Erlenmeyer flask was added 2-(4,5-diamino-1H-pyrazol-1-yl)ethan-1-ol sulfate (1.08 g, 4.5 mmol) and 3-amino-2,6-dimethylphenol (0.617 g, 4.5 mmol). To the mixture was then added water (50 mL), ethanol (10.0 mL) and 28% ammonium hydroxide aq. solution (5.0 mL) to completely dissolve the dye precursors. The tint solution turned light red. The K$_3$Fe(CN)$_6$ solution was then transferred to the flask containing the dye precursors. The solution immediately turned dark red. The reaction mixture was then magnetically stirred for 30 min. After which the reaction mixture was filtered, rinsed with water to yield 0.582 g of a dark red solid (47% yield). $^1$H NMR (300 MHz, DMSO-d$_6$): δ 1.77 (s, 3H), 1.94 (s, 3H), 3.70 (q, 2H, J=5.4 Hz), 3.98 (t, 2H, J=5.7 Hz), 4.96 (t, 1H, J=5.1 Hz), 6.29 (br, 2H), 6.58 (s, 2H), 7.17 (s, 1H), 7.73 (s, 1H). HRMS Found: [M+H]+ 276.1458; molecular formula C$_{13}$H$_{17}$N$_5$O$_2$ requires [M+H]+ 276.1455.

3.3.9 Formation of Azomethine Dyes and Measurement of Absorbance Maxima

For each primary intermediate-couple pair, 0.0625 M of the primary intermediate and coupler were dissolved in 75:20:5 water:ethanol:28% ammonium hydroxide mixture. An equal volume of 0.25 M aqueous K$_3$Fe(CN)$_6$ was added to the solution of dye precursors, giving rapid color formation. The reaction mixture was purified on a Waters Acuity™ UPLC with a PDA e, detector using a Cortecs,™ 1.6 µm, 2.1×100 mm UPLC® C18 reverse phase column using an water-acetonitrile linear gradient with a 0.4 mL/min flow rate, and the absorbance maximum of the pure compound was determined.

3.3.10 Determination of Extinction Coefficients

Compound 4, 16, 22, or 25c, the purity of which had been determined with qNMR with thymol as the internal reference, was dissolved in 5 w/w % aqueous ethanol to obtain a concentration of $10^{-4}$ M. The absorbance was measured at room temperature with a Cary 100 UV/visible spectrophotometer using a 1 cm path length cuvette, and was taken as the difference between the baseline and the absorbance at the $\lambda_{max}$. Extinction coefficient was determined as:

$$\varepsilon = A/cl$$

Where, $\varepsilon$ is the extinction coefficient, A is the absorbance at $\lambda_{max}$, and l is the cell path length.

3.3.11 Hair Dyeing Procedure

Primary intermediates and couplers for each experiment were dissolved in 75:20:5 water:ethanol:28% ammonium hydroxide prepare 100 mL of each primary intermediate-coupler pair at a concentration of 0.625 M each, as in Table 3. Ten mL of his solution was mixed with an equal volume of (commercial Wella™ colorcharm 20 Volume (6% $H_2O_2$) clear developer to give a solution at pH 10±0.2. This was applied to 1.5 g virgin natural white hair tresses so the hair:dye bath weight ratio was 1:6. The tresses were covered to prevent evaporation of solvent and ammonia, and placed in a 30° C. oven for thirty minutes. The tresses were rinsed with water and shampooed once with Pantene® Clarifying Shampoo to remove surface dye deposits. The tresses were dried with a hairdryer on low heat, and then color readings on duplicate tresses were obtained.

REFERENCES

[1] LeDuc M, Metais E, Sabelle S, Rondot, C. L'Oreal. Azomethine direct dyes or reduced precursors of azomethine direct dyes obtained from 2-alkylresorcinols, and hair dyeing process using these dyes or precursors. European Patent EP 2246038 B1, 2010 Apr. 28.
[2] Fadli A, Blais S. L'Oreal. Azomethine direct dyes or reduced precursors of azomethine direct dyes obtained from 2-alkylresorcinols, and hair dyeing process using these dyes or precursors. European Patent EP 2231586 B1, 2008 Dec. 9.
[3] Corbett J F. Benzoquinone Imines. Part IX. Mechanism and Kinetics of the Reaction of p-Benzoquinone Diimines with m-Aminophenols. J Chem Soc, Perkin Trans 2 1972:539-48.
[4] Morel O J X, Christie R M. Current Trends in the Chemistry of Permanent Hair Dyeing. Chem Rev 2011; 111(4):2537-61.
[5] Brody F, Burns M S. Studies Concerning the Reactions of Oxidation Dye Intermediates. J. Soc Cosmet Chem 1968; 19, 361-79.
[6] Corbett J F. The Role of Meta Difunctional Benzene Derivatives. J Soc Cosmet Chem 1973, 24:103-34.
[7] Bailey A D, Murphy B P, Guan H. Mechanistic Insights into Oxidative Oligomerization of p-Phenylenediamine and Resorcinol. J Phys Chem A 2016; 120:8512-20.
[8] Zollinger H. Color Chemistry: Syntheses, Properties, and Applications of Organic Dyes and Pigments. Third, revised edition. Weinheim and Zurich, Switzerland: Wiley-VCH, 2003,
[9] Murphy B P. Hair Colorants. In: Butler H, editor. Poucher's Perfumes, Cosmetics and Soaps, $10^{th}$ Ed, London: Kluwer Academic Publishers; 2000: p. 307-24.
[10] Bugaut A, Gallien J, Gascon J, Gaston-Breton H, Kalopissis G. L'Oreal. Dyeing human hair and composition for including an oxidation dye and heterocyclic coupler thereof. U.S. Pat. No. 3,712,158, 1973 Jan. 23.
[11] Corbett J F. Benzoquinone Imines. Part VI. Mechanism and Kinetics of the Reaction of p-Benzoquinone Diimines with m-Phenylenediamines. J Chem Soc (B) 1969; 827-35.
[12] Yin Y, Zheng, K, Eid N, Howard S, Jeong J-H, Yi F, Guo J, Park C M, Bibian M, Wu W, Hernandez P, Park H, Wu Y, Luo J-L, LoGrasso P V, Feng Y. Bis-aryl Urea Derivatives as Potent and Selective LIM Kinase (LIMK) Inhibitors. J Med Chem 2015; 58(4):1846-61.
[13] Katz S J, Bergmeier S C. Convenient methods for the hydrolysis of oxazolidinones to vicinal aminoalcohols. Tetrahedron Lett. 2002; 43(4):557-9.
[14] Miller A E. Catalytic process for converting 2-oxazolidinones to their corresponding alkanolamines. U.S. Pat. No. 4,514,379, 1985 Apr. 30.
[15] Cook F T, Baugh Jr D W, Chambers Jr R V. Monoalkyleneglycols, monoalkanolamines and alkylenediamine. U.S. Pat. No. 4,272,455, 1981 Jun. 9.
[16] Scientific Committee on Consumer Products (SCCS), Opinion on Intermediates and reaction products of oxidative hair dye ingredients formed during hair dyeing, SCCP/1198/08, Adopted at the 19th plenary meeting of 21 Jan. 2009.
[17] Scientific Committee on Consumer Products (SCCS), Opinion on Reaction Products of Oxidative Hair Dye Ingredients Formed during Hair Dyeing Processes, SCCS/1311/10, Adopted at the 8th plenary meeting of 21 Sep. 2010.
[18] Bugaut A, Junino A. L'Oreal. Dyeing compositions for hair which contain 2,4-diaminobutoxybenzene and/or a salt thereof as a coupling agent. U.S. Pat. No. 4,323,360, 1982 Apr. 6.
[19] Bugaut A, Shahin M, Vandenbossche J-J H, Kalopissis. L'Oreal. Meta-phenylenediamines, dyeing compositions in which they are present and the corresponding dyeing process. U.S. Pat. No. 4,333,730, Jun. 8, 1982.
[20] Kijek, J E, Brown, K C, Murphy B P. Clairol Incorporated. Hair dye coupler and process for making. U.S. Pat. No. 4,838,894, 1989 Jun. 13.

What is claimed is:

1. An oxidation dye coupler suitable for forming an azomethine dye and/or a leuco dye, comprising a compound of Formula I:

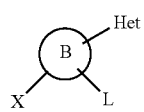

Formula I

Wherein
B is an aromatic ring selected from the group consisting of phenyl, pyridinyl, benzomorpholinyl, benzimidazolyl and indolyl;
X is H, OH, $NH_2$ or $NR^1H$;
L is $OR^5$;
$R^1$ is hydrogen, methyl or ethyl;
$R^5$ is hydrogen;
Het is selected from Formula A, B, C or D:

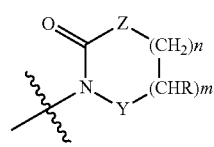

Formula A

-continued

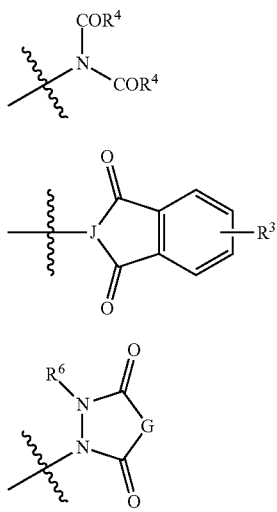

Y is C=O, CH$_2$;
Z is O, CH$_2$ or —R$^2$C=CR$^2$—;
J is N or —N—NR$^6$—;
G is (CHR$^6$)$_p$, —R$^2$C=CR$^2$—;
n is zero or an integer of 1 to 6;
m is zero or an integer of 1 to 6;
p is an integer of 1 to 3;
At least one of m and n is 1 unless Z is —R$^2$C=CR$^2$—;
Each R independently is hydrogen, linear or branched alkyl of 1 to 6 carbons, cyclic alkyl of 3 to 6 carbons, linear or branched alkoxy of 1 to 6 carbons, alkylalkoxy of 1 to 4 carbons in the alkyl group and 1 to 4 carbons in the alkoxy group, alkylamino of 1 to 4 carbons in the alkyl group or aminoalkyl of 1 to 4 carbons in the alkyl group;
Each R$^2$ independently is hydrogen or a linear or branched alkyl of 1 to 4 carbons;
R$^3$ is hydrogen, a linear or branched alkyl of 1 to 6 carbons or a cyclic alkyl of 3 to 6 carbons;
Each R$^4$ independently is a linear, branched alkyl of 1 to 6 carbons, a cyclic alkyl of 3 to 6 carbons, a linear or branched hydroxyalkyl of 1 to 6 carbons, a cyclic hydroxyalkyl of 3 to 6 carbons, phenyl, toluenyl or pyridinyl;
Each R$^6$ independently is hydrogen, methyl or ethyl; and
The squiggle bond of Het indicates the bond between Het and the B aromatic ring.

2. A coupler according to claim 1 wherein Formula I is selected from any one of Formulas IA to IE:

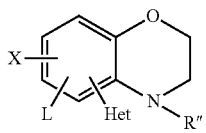

IA

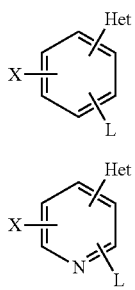

IB

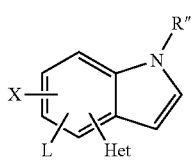

IC

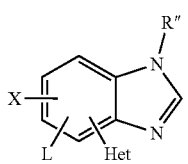

ID

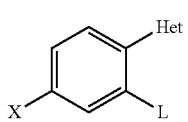... wait

Formula B
Formula C
Formula D

IC
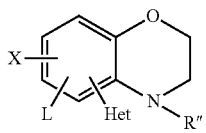

ID
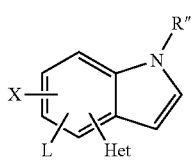

IE
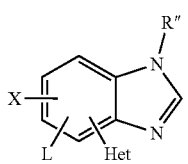

And each R″ independently is hydrogen, a linear, branched alkyl of 1 to 6 carbons, a cyclic alkyl of 3 to 6 carbons, a linear or branched hydroxyalkyl of 1 to 6 carbons, a cyclic hydroxyalkyl of 3 to 6 carbons or phenyl.

3. A coupler according to claim 2 wherein Formulas IA-IE are:

IA
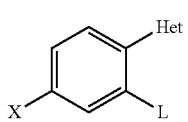

IB
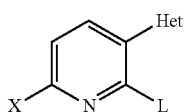

IC
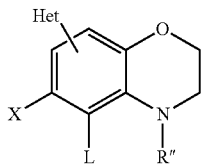

ID
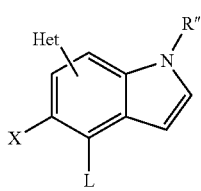

IE
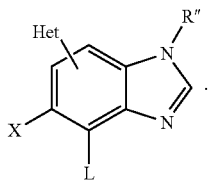

4. A coupler of claim 2 wherein Formula I is Formula IA, IB or ID.

5. A coupler of claim 4 wherein Formula I is Formula IA and Het is Formula A, Formula C or Formula D.

6. A coupler of claim 5 wherein Het is Formula A.

7. A coupler of claim 6 wherein Z is O or CH$_2$; m is zero or 1; n is zero or 1 and the sum of m and n is 1 or 2.

8. A coupler of claim 7 wherein Z is O, m is zero and n is 1.

9. A coupler of claim 5 wherein Het is Formula C.

10. A coupler of claim 9 wherein Het is phthalimidyl.

11. A coupler of claim 5 wherein Het is Formula D.

12. A coupler of claim 11 wherein Het is

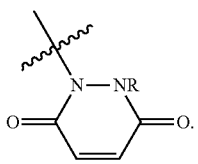

13. An azomethine dye of Formula IIa or a leuco dye or Formula IIb

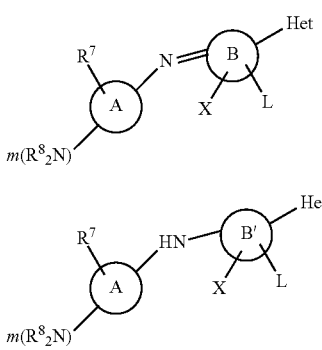

Wherein

A is an aromatic ring selected from the group consisting of phenyl, pyrazolyl, benzimidazolyl, pyrrolopyridinyl, benzoxazinyl and dihydroprazolopyrazolonyl;

$R^7$ is hydrogen, hydroxyl, linear or branched alkyl of 1 to 6 carbons, cyclic alkyl of 3 to 6 carbons, linear or branched hydroxyalkyl of 1 to 6 carbons, cyclic hydroxyalkyl of 3 to 6 carbons, linear or branched alkoxy of 1 to 6 carbons, cyclic alkoxy of 3 to 6 carbons, linear or branched alkoxyalkyl of 1 to 4 carbons in the alkoxy group and 1 to 4 carbons in the alkyl group, cyclic alkoxyalkyl of 1 to 4 carbons in the alkoxy group and 3 to 6 carbons in the alkyl group, or linear or branched hydroxyalkoxy of 1 to 6 carbons in the alkoxy group;

Each $R^8$ independently is hydrogen, hydroxyalkyl of 1 to 4 carbons, N,N-di-(hydroxyalkyl)aminoalkyl of 1 to 3 carbons in each hydroxyalkyl group and 1 to 3 carbons in the alkyl group;

m is zero or one;

B is a di-hydro aromatic ring of Formula IIa selected from the group consisting of di-hydro forms of phenyl, pyridinyl, benzimidazolyl, benzomorpholinyl and indolyl;

B' is an aromatic ring of Formula IIb selected from the group consisting of phenyl, pyridinyl, benzimidazolyl, benzomorpholinyl and indolyl;

The N═ moiety is an imine group with the double bond attached directly to a carbon of the B ring of Formula IIa;

The —NH— moiety is an amine group attached directly to a carbon of the B' ring of Formula IIb;

X is OH, NH$_2$ or NRH;

L is ═O of Formula IIa;

L' is OH of Formula IIb;

Het is selected from Formula A, B, C or D:

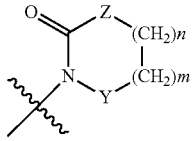
Formula A

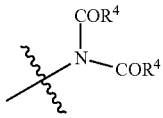
Formula B

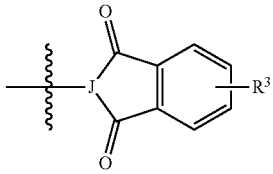
Formula C

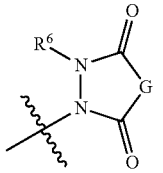
Formula D

Y is C═O, CH$_2$;

Z is O, CH$_2$ or —$R^2$C═C$R^2$—;

J is N or —N—N$R^6$—;

G is (CH$R^6$)$_p$, —$R^2$C═C$R^2$—;

n is zero or an integer of 1 to 6;

m is zero or an integer of 1 to 6;

p is an integer of 1 to 3;

At least one of m and n is 1 unless Z is —$R^2$C═C$R^2$—;

Each R independently is hydrogen, linear or branched alkyl of 1 to 6 carbons, cyclic alkyl of 3 to 6 carbons, linear or branched alkoxy of 1 to 6 carbons, alkylalkoxy of 1 to 4 carbons in the alkyl group and 1 to 4 carbons in the alkoxy group, alkylamino of 1 to 4 carbons in the alkyl group or aminoalkyl of 1 to 4 carbons in the alkyl group;

Each $R^2$ independently is hydrogen or a linear or branched alkyl of 1 to 4 carbons;

$R^3$ is hydrogen, a linear or branched alkyl of 1 to 6 carbons or a cyclic alkyl of 3 to 6 carbons;

Each $R^4$ independently is a linear, branched alkyl of 1 to 6 carbons, a cyclic alkyl of 3 to 6 carbons, a linear or branched hydroxyalkyl of 1 to 6 carbons, a cyclic hydroxyalkyl of 3 to 6 carbons, phenyl, toluenyl or pyridinyl;

Each $R^6$ independently is hydrogen, methyl or ethyl; and

The squiggle bond of Het indicates the bond between Het and the B aromatic ring.

14. An azomethine dye of Formula IIa of claim 13.

15. A leuco dye of Formula IIb of claim 13.

16. An azomethine dye or a leuco dye of claim 13 wherein when R⁷ is OH, m is zero and when m is 1, R⁷ is other than OH and at least one of R⁸ is hydrogen.

17. An azomethine dye or leuco dye of claim 13 wherein the precursor of the A ring and its substituents is a developer of any one of Formulas IV-IX wherein the pair of groups: a) NH₂ and R⁷ as OH and b) NH₂ and R⁸₂N are positioned on Formulas IV-IX at any position relative to each other except a meta position and the group R⁷ or R⁸₂N that is not part of the pair is positioned at any other position on the A ring:

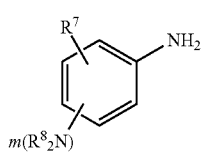

Formula IV

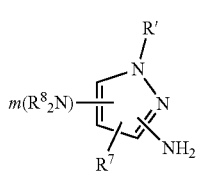

Formula V

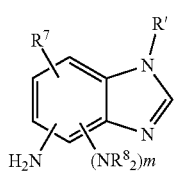

Formula VI

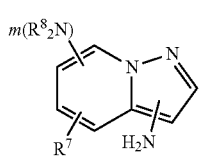

Formula VII

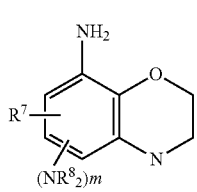

Formula VIII

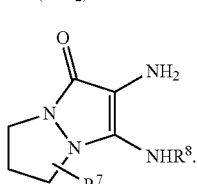

Formula IX

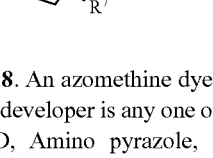

18. An azomethine dye or leuco dye of claim 13 wherein the developer is any one of Formulas PAP, Bis, PPD, Alkoxy PPD, Amino pyrazole, hexyl pyrazole, Pyrrolopyridine, Hydroxy PPD, Benzomopholine PPD, Methoxy, hydroxyl PPD and dihydro PPZO, wherein R''' of Benzomopholine PPD is hydrogen, alkyl of 1 to 4 carbons or phenyl and R^iv of Benzomopholine PPD is hydrogen, alkyl of 1 to 4 carbons, alkoxy of 1 to 4 carbons, alkylalkoxy of 1 to 4 carbons in each of the alkyl and alkoxy groups, or hydroxyalkyl of 1 to 4 carbons in the alkyl group:

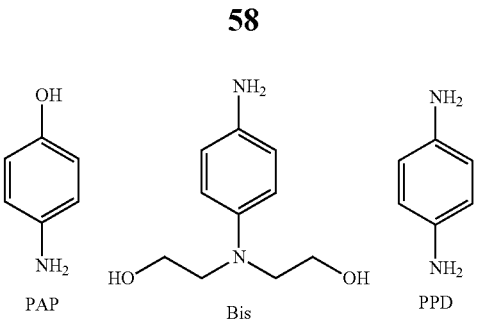

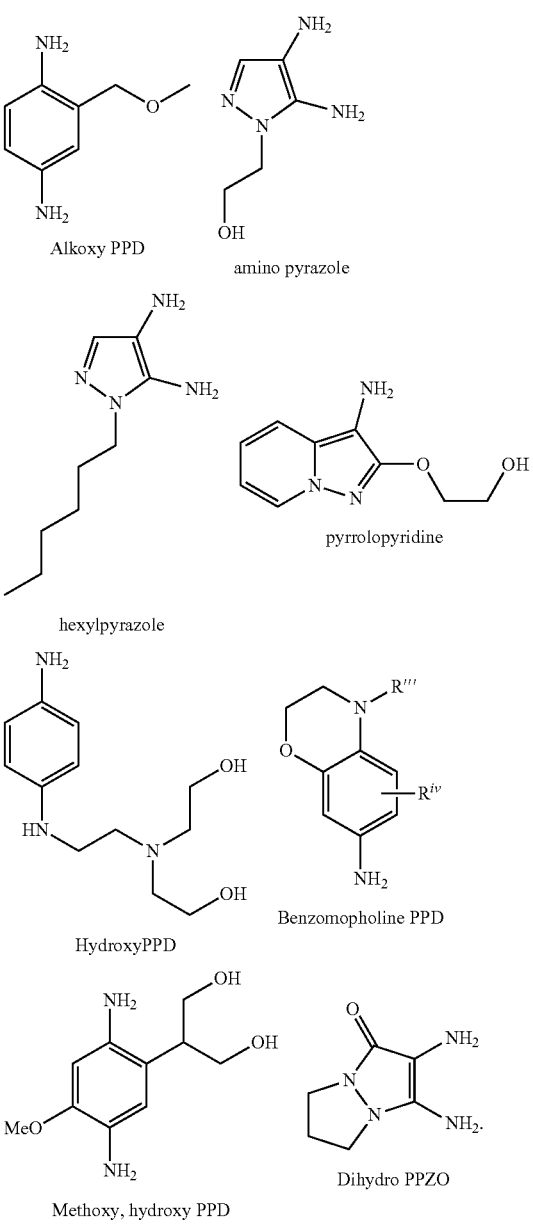

19. An azomethine dye or leuco dye of claim 13 wherein precursor of the B ring and its substituents and the B' ring and its substituents is a coupler of any one of Formulas IA to IE wherein each R'' independently is hydrogen, a linear, branched alkyl of 1 to 6 carbons, a cyclic alkyl of 3 to 6 carbons, a linear or branched hydroxyalkyl of 1 to 6 carbons, a cyclic hydroxyalkyl of 3 to 6 carbons or phenyl:

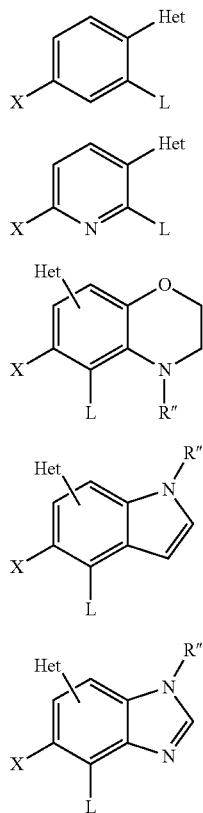

IA
IB
IC
ID
IE

20. An azomethine dye or leuco dye of claim 19 wherein the coupler is Formula IA, IB or ID.

21. An azomethine dye or leuco dye of claim 20 wherein the coupler is Formula IA and Het is Formula A, Formula C or Formula D.

22. An azomethine dye or leuco dye of claim 21 wherein Het is Formula A.

23. An azomethine dye or leuco dye of claim 22 wherein Z is O or $CH_2$; m is zero or 1; n is zero or 1 and the sum of m and n is 1 or 2.

24. An azomethine dye or leuco dye of claim 23 wherein Z is O, m is zero and n is 1.

25. An azomethine dye or leuco dye of claim 21 wherein Het is Formula C.

26. An azomethine dye or leuco dye of claim 25 wherein Het is phthalimidyl.

27. An azomethine dye or leuco dye of claim 21 wherein Het is Formula D.

28. An azomethine dye or leuco dye of claim 21 wherein Het is

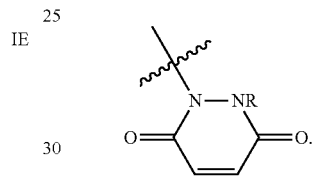

\* \* \* \* \*